(12) United States Patent
Eden

(10) Patent No.: US 7,520,975 B2
(45) Date of Patent: Apr. 21, 2009

(54) ESTIMATION OF LOCALISED CORROSION PENETRATION

(75) Inventor: David Anthony Eden, Spring, TX (US)

(73) Assignee: Honeywell International Inc., Morristown, NJ (US)

( * ) Notice: Subject to any disclaimer, the term of this patent is extended or adjusted under 35 U.S.C. 154(b) by 912 days.

(21) Appl. No.: 10/471,643

(22) PCT Filed: Mar. 8, 2002

(86) PCT No.: PCT/GB02/01057

§ 371 (c)(1),
(2), (4) Date: Mar. 24, 2004

(87) PCT Pub. No.: WO02/073169

PCT Pub. Date: Sep. 19, 2002

(65) Prior Publication Data

US 2004/0149594 A1 Aug. 5, 2004

(30) Foreign Application Priority Data

Mar. 8, 2001 (GB) ................. 0105688.6

(51) Int. Cl.
*G01N 27/26* (2006.01)
(52) U.S. Cl. .................. 205/775.5; 205/777

(58) Field of Classification Search .......... 205/775, 205/775.5, 777; 204/404
See application file for complete search history.

(56) References Cited

U.S. PATENT DOCUMENTS 6,015,484 A * 1/2000 Martinchek et al. ...... 205/775.5

* cited by examiner

*Primary Examiner*—Alex Noguerola
(74) *Attorney, Agent, or Firm*—Adams & Reese LLP

(57) ABSTRACT

The present invention provides a method and apparatus for estimation of general and localized corrosion penetration rates of metallic materials and objects. The invention can also be used to discriminate between general and localized corrosion. A one, two or three electrode probe having electrodes (101, 102, 103) made of the same material as the material being monitored is located in the same corrosive environment as the material being monitored. An electrochemical harmonic analysis is performed and electrochemical noise signals are monitored, and the resulting responses are analyzed and compared to discriminate between general and localized corrosion attack and to determine a localized corrosion penetration rate. A law frequency sine wave is applied to the working electrode. Harmonic analysis of the electrode response provides information regarding the general corrosion rate and the stern-geary constant. Electrochemical noise analysis of the electrode response and comparison with harmonic data provides a means of determination of localized corrosion penetration rate.

42 Claims, 15 Drawing Sheets

US 7,520,975 B2

ESTIMATION OF LOCALISED CORROSION PENETRATION

This application is a 371 of PCT/GB02/01057, filed Mar. 08, 2002, which claims priority from United Kingdom application 0105688.6, filed on Mar. 08, 2001.

DESCRIPTION OF THE RELATED ART

The present invention relates to a method for estimation of localised corrosion penetration, in particular pitting corrosion, which occurs on a metal surface when exposed to corrosive environments. The invention provides means for detecting corrosion and discriminating between general and localised corrosion mechanisms, and can provide estimates of general and localised corrosion rates. The present invention typically utilises a plurality of electrochemical techniques on the same set of electrodes, principally electrochemical noise and harmonic distortion analysis, to detect general and localised corrosion processes. Comparison of the analysed data from the electrochemical techniques provides information regarding the type and penetration rate of corrosion.

Electrochemical noise (ECN) has been used for the monitoring of both general and localised corrosion, and methods and apparatus for analysing and collating ECN signals have been described in U.S. Pat. Nos. 4,575,678, 5,139,627 and 6,015,484. U.S. Pat. No. 4,575,678 refers to a methodology for monitoring and analysing potential noise signals originating from corrosion processes.

U.S. Pat. No. 5,139,627 refers to monitoring current noise signals between identical electrodes using a Zero Resistance Ammeter (ZRA), and evaluation of the system propensity to localised corrosion by comparing the standard deviation of the current with the mean measured current. This latter methodology may give spurious indications if the mean current attains values that drift through zero. U.S. Pat. No. 6,015,484 claims to improve on the latter method by applying a dc bias to the electrodes to prevent the zero crossing. Eden et al[4] proposed a general theoretical relationship between the electrochemical noise signals and the Stern-Geary constant. Testing of the latter relationship has hitherto been experimentally difficult; the relationship between measured Stern-Geary values and electrochemical noise signals has previously been difficult to ascertain in real systems. It has been found that the experimentally determined Stern-Geary values and electrochemical noise signals derived from the same electrode arrangement can provide an indication of the localised corrosion penetration rate.

BRIEF SUMMARY OF THE INVENTION

According to a first aspect of the present invention, there is provided a method of assessing corrosion of a metal object, the method comprising the steps of
providing the metal object with an electrode assembly capable of generating electrochemical noise signals, the electrode assembly including at least one electrode that is electrically isolated from the metal object;
periodically sampling the electrochemical noise signals;
applying a signal to the electrode assembly and obtaining a current response of the electrode assembly; and
analysing the statistical distribution of the noise signals and a harmonic content of the current response to determine information concerning the corrosion.

The method typically allows the extent of the corrosion to be assessed. Alternatively, or additionally, the method allows the nature of the corrosion to be assessed.

The method typically includes a comparison of the harmonic content analysis of the current response and the statistical distribution of the noise signals.

Preferably, the electrode assembly includes three electrodes. Where three electrodes are used, the electrodes are typically electrically isolated from one another.

The or each electrode is preferably of substantially the same composition as the metal object. Alternatively, or additionally, the or each electrode is preferably of substantially the same state as the metal object. Preferably, the or each electrode is exposed to the same corrosive environment as the metal object.

Preferably, no potential is applied to the or each electrode during the generation and sampling of the electrochemical noise signals.

Where three electrodes are used, a first electrode is preferably maintained at a potential of zero volts with respect to a second electrode during the generation and sampling of the electrochemical noise signals.

The step of periodically sampling the current noise signal typically comprises the step of periodically measuring a current flowing between the first electrode and the third electrode.

Optionally, the second and third electrodes can be combined into a single electrode that is of substantially greater surface area than the first electrode. In this embodiment, the single electrode can comprise the metal object.

The method typically includes the additional step of calculating a first, second, third and/or fourth moment of the current noise signal. The method optionally includes the additional step of calculating parameters of the current noise signal, the parameters being selected from the group consisting of kurtosis and skewness values. The method preferably includes the additional step of calculating a standard deviation of the current noise signal.

The step of periodically sampling the potential noise signal typically comprises the step of periodically measuring a potential difference between the first electrode and a third electrode. The method typically includes the additional step of calculating a first, second, third and/or fourth moment of the potential noise signal. The method optionally includes the additional step of calculating parameters of the potential noise signal, the parameters being selected from the group consisting of kurtosis and skewness values.

The method preferably includes the additional step of calculating a standard deviation of the potential noise signal.

The signal that is applied to the electrode assembly typically comprises a low frequency, low voltage sinusoidal wave. The frequency is typically in the range of 0.001 Hertz to 1 Hertz, although the frequency can be outwith this range. The voltage is typically in the range of 20 to 60 millivolts peak to peak, although it can be outwith this range. The signal can be given by $V \sin \omega t$.

The signal is typically applied between a first and a second electrode. The current response is typically obtained by measuring a current flowing between the first and a third electrode in response to the applied signal.

The analysis of the harmonic content preferably includes the additional step of sampling the current response at periodic intervals.

The step of analysing the harmonic content typically includes the step of calculating a first harmonic content of the current response. Calculating the first harmonic typically includes the additional steps of multiplying the measured current response obtained at each sample by $\sin 2\pi ft$ (where f is the frequency of the signal and t is the time at which the current response was sampled) for each time period; summing all of the multiplications; and dividing by the total number of samples taken. This provides an average value of the first harmonic content.

The method preferably includes the additional step of comparing the first harmonic of the current response with the standard deviation of the current noise signal (i.e. the square root of the second moment of the current noise signal). The comparison can be used to differentiate between localised and general corrosion.

Analysing the harmonic content typically includes the step of calculating a second harmonic content of the current response. Calculating the second harmonic typically includes the additional steps of multiplying the measured current response obtained at each sample by $-\cos(2)(2\pi ft)$ (where f is the frequency of the signal and t is the time at which the current response was sampled) for each time period; summing all of the multiplications; and dividing by the total number of samples taken. This provides an average value of the second harmonic content.

The method typically includes the additional step of comparing the second harmonic of the current response (rectification current) with the first moment of the current noise signal (the mean current). The comparison can be used to differentiate between localised and general corrosion.

Optionally, the step of analysing the harmonic content includes the step of calculating a third harmonic content of the current response.

Calculating the third harmonic typically includes the additional steps of multiplying the measured current response obtained at each sample by $-\sin(3)(2\pi ft)$ (where f is the frequency of the signal and t is the time at which the current response was sampled) for each time period; summing all of the multiplications; and dividing by the total number of samples taken. This provides an average value of the third harmonic content.

The method preferably includes the additional step of calculating a corrosion current derived from the harmonic analysis. Preferably, the method includes the additional step of comparing the corrosion current to the standard deviation of the current noise signal. This comparison can be used to provide an estimation of the localised corrosion penetration rate.

The method preferably includes the additional step of calculating anodic and cathodic Tafel constants from the harmonic analysis. The method preferably includes the additional steps of calculating a Stern-Geary constant from the harmonic analysis. The Stern-Geary constant is typically derived from the Tafel constants. The Stern-Geary constant is typically derived by multiplying the anodic and cathodic Tafel constants together, and then dividing by the sum of the anodic and cathodic Tafel constants.

The method preferably includes the additional step of comparing the Stern-Geary constant to the standard deviation of the potential noise signal. The comparison can provide an estimation of the localised corrosion penetration rate.

The method preferably includes the additional step of calculating a corrosion rate. The corrosion rate is typically proportional to the corrosion current.

The method preferably includes the additional step of calculating a factor $E_c$. The factor $E_c$ is typically calculated by dividing the standard deviation of the current noise signal by the corrosion current. The method preferably includes the additional step of modifying the value of the corrosion current by multiplying the value by a scaling factor of $E_c/0.001$.

The method preferably includes the additional step of re-calculating the corrosion rate using the modified value of the corrosion current.

The method preferably includes the additional step of calculating a factor $E_p$. The factor $E_p$ is typically calculated by dividing the standard deviation of the potential noise signal by the Stern-Geary constant.

The method preferably includes the additional step of modifying the value of the corrosion current by multiplying the value by a scaling factor of $E_p/0.001$. The method preferably includes the additional step of calculating a corrosion rate using the modified value of the corrosion current.

The values of $E_c$ and $E_p$ are typically equal and are also referred to as a composite value E. The value E is a system dependent constant that can be used to characterise the corrosion process as the value of this is different for localised and general corrosion.

The scaling factor takes into account that the corrosion may not be general corrosion that is over the entire surface area of the electrode, but is localised corrosion that is concentrated in one or more particular areas. Multiplying the corrosion current by this scaling factor gives an improved estimate of the corrosion current because it takes into account that the corrosion current may be related to general or localised corrosion. The improved value of the corrosion current can then be used to provide an indication of the localised penetration rate.

One embodiment of the present invention comprises a three-electrode sensor, of substantially the same material as the vessel or pipework, exposed to the corrosive environment. In this embodiment the data acquisition and analysis is time multiplexed, using alternate electrochemical noise and harmonic analysis techniques. In the first phase, the current is measured with the potential between a reference electrode and a working electrode set to 0 volts. The potential between an auxiliary electrode and the working electrode is measured simultaneously. Time series data (that is raw data) are analysed statistically to provide the first, second, third, and fourth moments of the current and potential noise signals. A minimum number of 100 discrete measurements are advisable for statistical analysis, although the number of measurements taken is not essential. It will be noted that the more measurements that are taken, the more representative the results will be.

In the second phase, a low frequency (0.001 to 0.1 Hertz) sinusoidal voltage of between 20 to 60 millivolts (mV) peak to peak is applied, and the current response analysed for the harmonic distortion components, namely, the first, second and third harmonic components, using single sine Fourier analysis techniques. Further derivatives of the statistical analysis of the potential and current noise signal moments are calculated, those typically being the mean (first moment), standard deviation (square root of the second moment), skewness (obtained by dividing the third moment by the second moment raised to the power 1.5, that is $M3/((M2)^{1.5})$, and kurtosis (obtained by dividing the fourth moment by the second moment raised to the power 2, that is $M4/((M2)^2)$. Further derivatives of the harmonic distortion measurements, namely, anodic and cathodic Tafel constants, the Stern-Geary constant and the corrosion current ($I_{corr}$) are also derived.

In preferred embodiments of the present invention, the results of the electrochemical noise and harmonic distortion analyses are compared to provide an improved method for detection of and estimation of penetration rates of localised and general corrosion.

A number of means may be used independently, or in combination, to indicate if the corrosion processes are localised or general.

In this embodiment, comparison of the rectification current (second current harmonic) with the mean current (first moment current noise measurement) may be used to differentiate between localised and general corrosion. Alternatively, comparison of the first current harmonic with the current standard deviation (square root of the second moment) may be used.

A preferred embodiment is the comparison of the corrosion current derived from harmonic distortion analysis with the current standard deviation (two or three electrode operation), or (in the three-electrode mode) the Stern-Geary value obtained from harmonic analysis with the potential standard deviation (which leads to the same result). The latter information may then be used to provide an estimation of the localised corrosion penetration rate.

According to a second aspect of the present invention, there is provided an improved method for discriminating between general and localised corrosion of a material surface exposed to a corrosive environment, the method comprising the steps of; providing the metal surface with an electrode assembly, the electrode assembly including three electrodes that are electrically isolated from one another and the metal surface; statistically analysing current and potential signals obtained when a first electrode is maintained at a potential of zero volts with respect to a second electrode; performing harmonic distortion analysis of a current signal obtained during application of a low amplitude, low frequency sine wave voltage signal between the first and second electrodes; producing a first signal that represents a comparison between a first moment (mean) of the current signal and a second current harmonic (rectification current) to indicate a degree of localisation of corrosion; producing a second signal that represents a comparison between a square root of the second moment (the standard deviation) and a first current harmonic to indicate a degree of localisation of corrosion; producing a third signal that represents a comparison between a square root of a second moment of the current signal (the standard deviation of current) and a corrosion current to indicate a degree of localisation of corrosion; and producing a fourth signal that represents a comparison between a square root of a second moment of the potential signal (standard deviation of potential) and a Stern-Geary constant (B) to indicate degree of localisation of corrosion.

The method typically includes one, some or all of the additional steps of determining a general corrosion rate from harmonic distortion analysis; and modifying the general corrosion rate estimate to provide an estimate of localised corrosion penetration rate. The third signal is typically used in modifying the general corrosion rate estimate.

Alternatively or additionally, the fourth signal is used to modify the general corrosion rate.

According to a third aspect of the present invention, there is provided a method for discriminating between general and localised corrosion of a material surface exposed to a corrosive environment, the method comprising the steps of; providing the metal surface with an electrode assembly, the electrode assembly including three electrodes that are electrically isolated from one another and the metal surface; performing harmonic distortion analysis on a current signal obtained during application of a low amplitude, low frequency sine wave voltage signal between a first electrode and a second electrode; performing statistical processing of the current signal obtained; producing a first signal that represents a comparison between a first moment (mean) of the current signal and a second current harmonic (rectification current) to indicate a degree of localisation of corrosion; producing a second signal that represents a comparison between a square root of a second moment (the standard deviation) and a first current harmonic to indicate a degree of localisation of corrosion; producing a third signal that represents a comparison between a square root of a second moment of current (the standard deviation of current) and a corrosion current to indicate a degree of localisation of corrosion.

The method typically includes the additional steps of; determining a general corrosion rate from the harmonic distortion analysis; and using the third signal to modify the general corrosion rate estimate to provide an estimate of localised corrosion penetration rate.

BRIEF DESCRIPTION OF THE SEVERAL VIEWS OF THE DRAWINGS

Embodiments of the present invention shall now be described, by way of example only, with reference to the accompanying drawings, in which:—

DETAILED DESCRIPTION OF THE INVENTION

Figure 1:
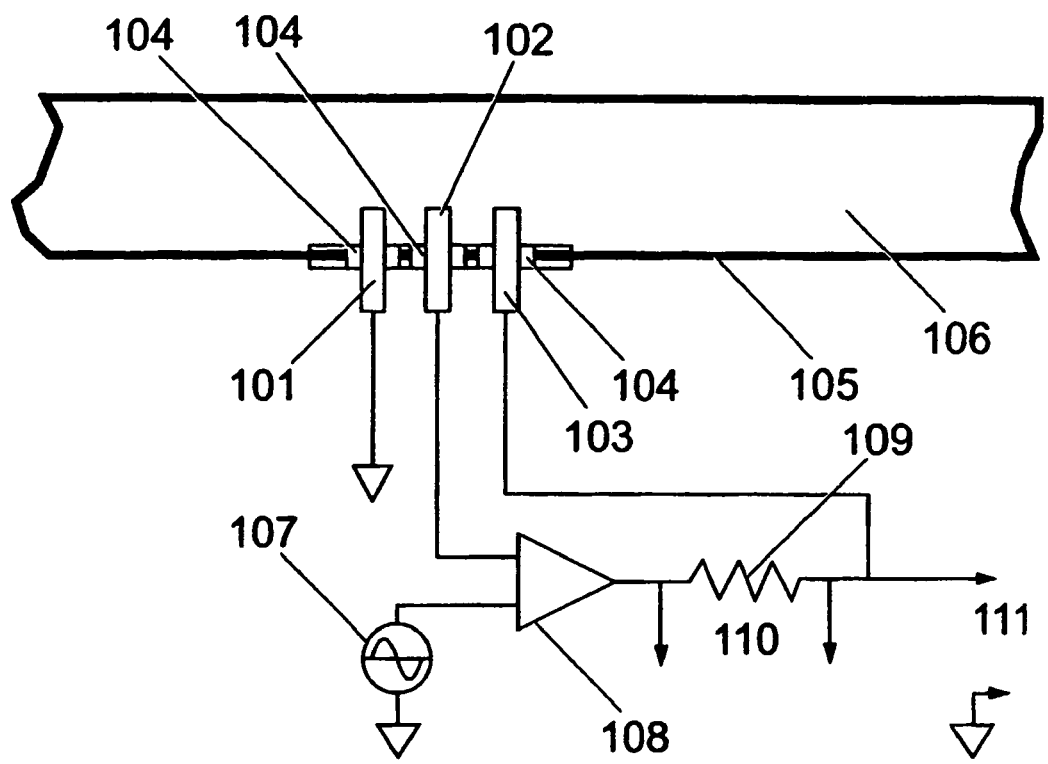
FIG. 1 is a schematic representation of a three-electrode cell for use with the present invention attached to a portion of plant that is to be monitored.

Referring to the drawings, FIG. 1 shows a portion of plant 105 that is to be monitored for corrosion so that the corrosion mechanism and/or the extent of the corrosion can be determined. The plant 105 can be any metal object such as a portion of a drill rig, a pipeline or any other metallic structure that is in a corrosive environment. In the embodiment shown, the plant 105 comprises a pipeline that typically has corrosive fluids flowing therein, or is otherwise exposed to a corrosive environment (e.g. located under water).

The embodiment in FIG. 1 illustrates a three-electrode cell, with three electrodes 101, 102 and 103 that represent three elements of a corrosion monitoring probe that is inserted into or otherwise attached to plant 105. The electrodes 101, 102, 103 are preferably of the same material as the plant 105, and are electrically isolated from one another by insulators 104. Thus, the electrodes 101, 102, 103 are exposed to the same environment (generally designated 106 in FIG. 1) as the material of the plant 105. The electrodes 101, 102, 103 are interfaced to an electrochemical monitoring system that includes a potentiostat 108. A means 107 of controlling the potential of electrode 101 with respect to electrode 102 is also provided, such as a variable power supply that has the capability to vary the voltage amplitude and frequency, particularly at lower values of amplitude and frequency. A resistor 109 is used to measure the current flowing through the three-electrode cell, that is output 110 is a measure of the voltage or potential across the resistor 109 and as the resistance of resistor 109 is known, the current flowing through the electrode cell can be calculated using Ohm's law. The driving potential across the electrodes 101, 102, 103 is measured and is output 111.

The cell shown in FIG. 1 is preferably used to take electrochemical noise (ECN) measurements and electrochemical harmonic distortion analysis (ECHD) measurements. During ECN measurements, the potential of the electrode 101 (with respect to electrode 102) is set to zero volts (0V) using means 107 that controls the potential of electrode 101 (with respect to electrode 102). Current noise measurements are then made by measuring the voltage across resistor 109 at output 110. Potential noise measurements are also taken across output 111.

Figure 2:
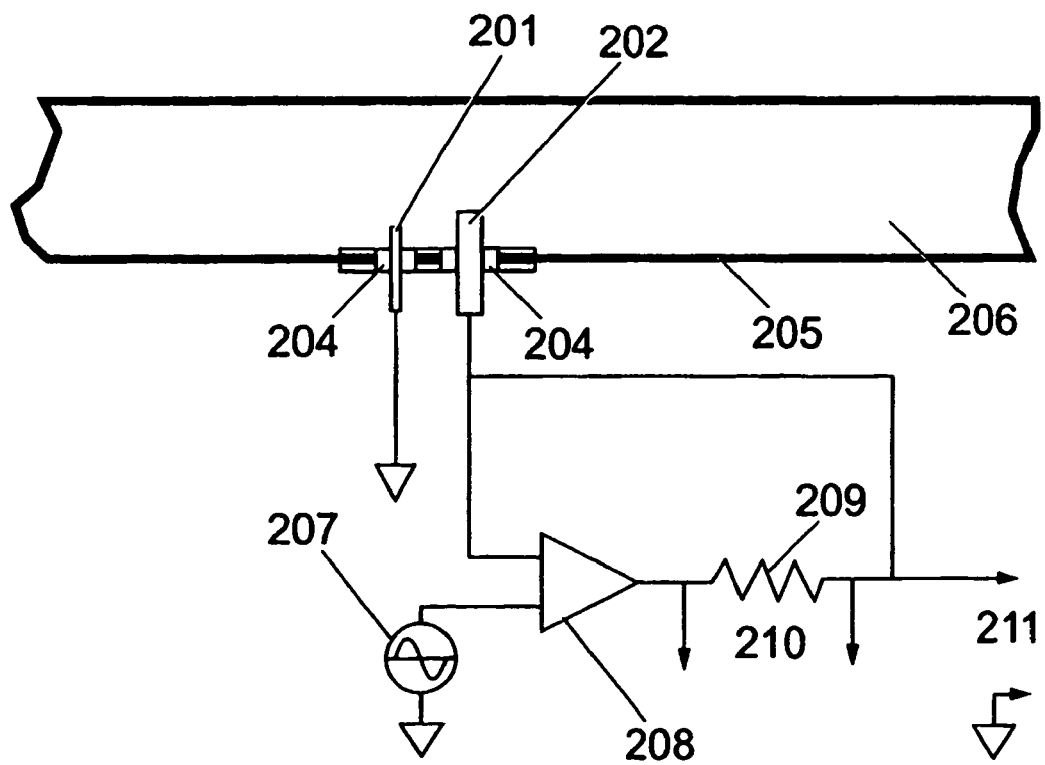
FIG. 2 is a schematic representation of an alternative embodiment of a two-electrode cell attached to a portion of plant that is to be monitored.

FIG. 2 shows a similar system to FIG. 1, except that only two electrodes 201, 202 are used for the ECN and ECHD measurements. Like components have been designated with the same reference numeral, but prefixed "2" instead of "1". Where only two electrodes are used, as with the embodiment shown in FIG. 2, it is preferable to have the electrodes 201, 202 with substantially different surface areas (as schematically shown). For example, the surface area of electrode 202 is typically in the order of 10 times the surface area of electrode 201.

Figure 3:
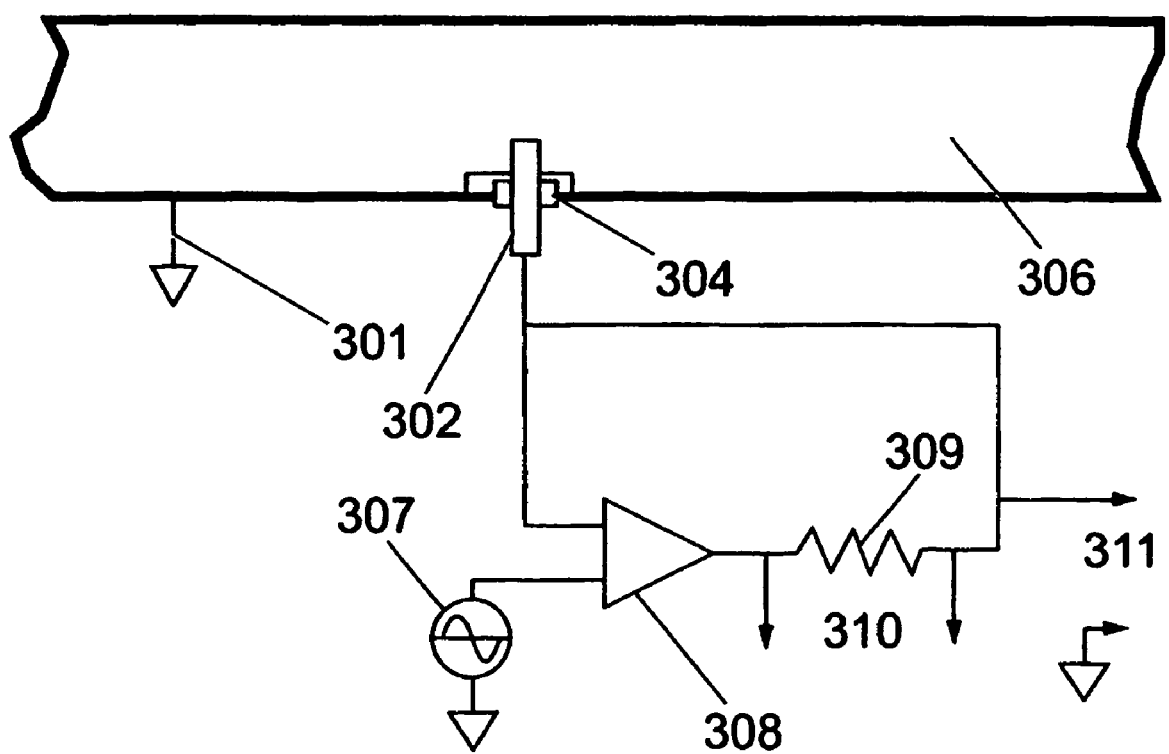
FIG. 3 is schematic representation of a further alternative embodiment of a one-electrode cell attached to a portion of plant that is to be monitored.

Referring to FIG. 3, there is shown a single-electrode cell that can be used with the method of the present invention. The single-electrode cell is similar to those shown in FIGS. 1 and 2 except that the plant 306 is used as a second electrode. In this particular embodiment, electrode 302 is substantially smaller in surface area than the plant 301.

Figure 4:
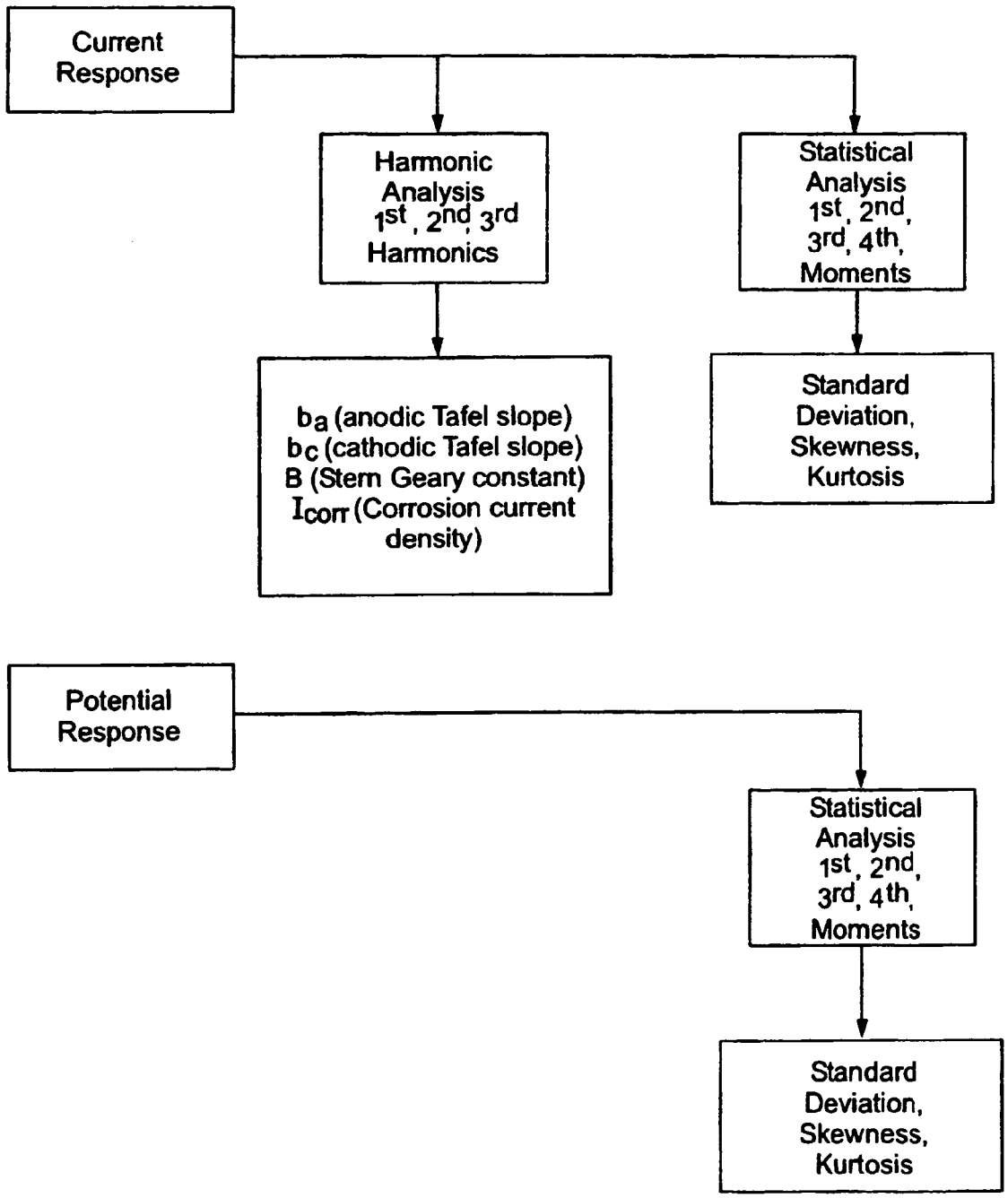
FIG. 4 is a flow diagram showing the processing that is done to the raw data collected by any of the cells of FIGS. 1 to 3.

In all the embodiments shown in FIGS. 1 to 3, potential and current noise measurements are made using a high resolution (typically in the order of 20 bits or more) analogue-to-digital converter and the data is analysed using the steps illustrated in FIG. 4. The signal from the analogue-to-digital converter is typically fed to a microprocessor that is used to control the potential of electrode 101 (with respect to electrode 102), and also to perform various control and communication functions, and can also perform the calculations, as will be described.

Figure 15:
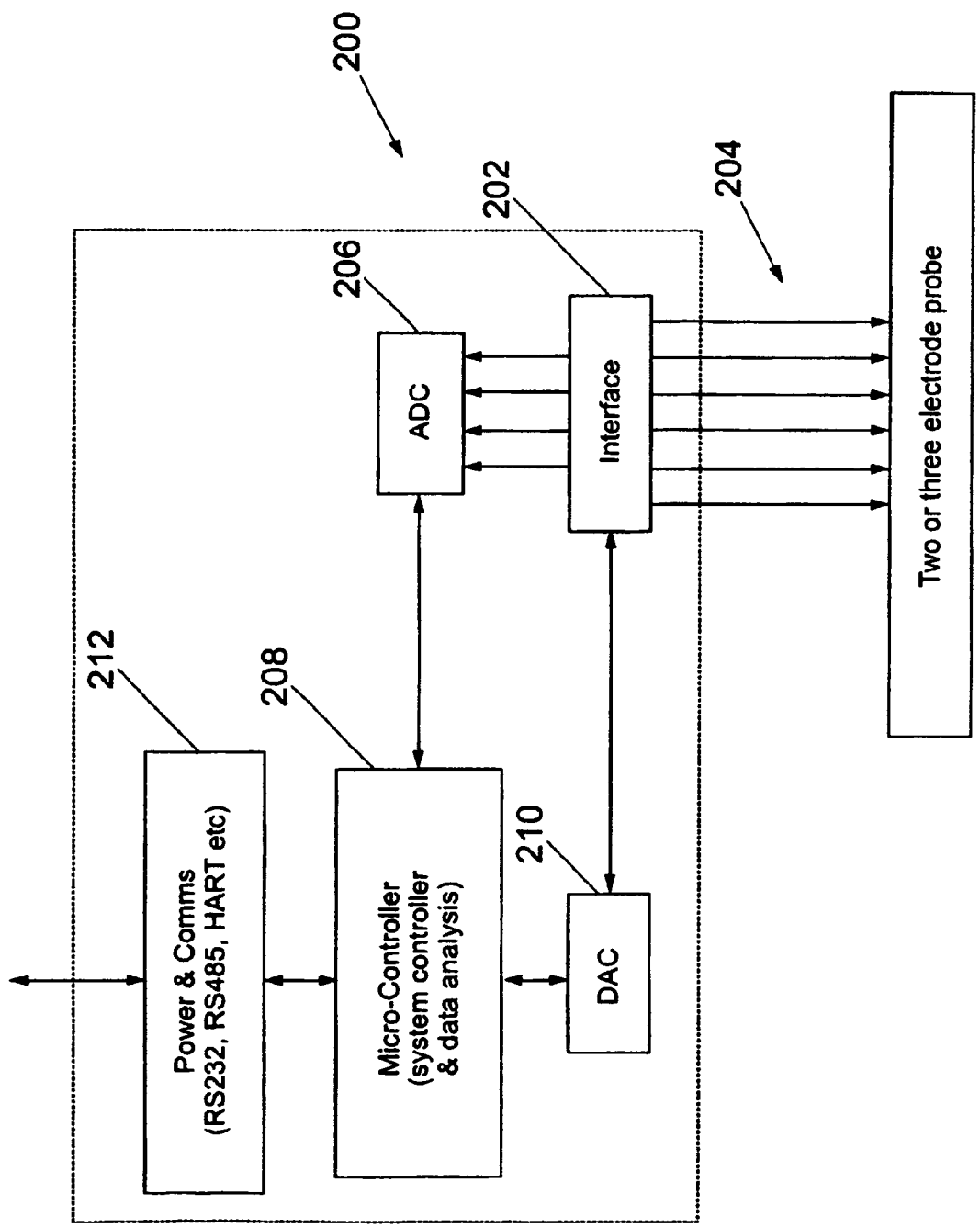
FIG. 15 is a schematic representation of an apparatus that can be used to collect data from the electrode cells of FIGS. 1 to 3.

Referring to FIG. 15, there is shown a schematic representation of apparatus 200 that can be used to collect the data from the electrode cells of FIGS. 1 to 3. The apparatus 200 includes an interface 202 that couples the signals from the electrodes in the cells of FIGS. 1 to 3 to the apparatus 200, via a plurality of wires or cables, generally designated 204.

The signals from the electrodes are then coupled to an analogue-to-digital converter 206. As is known in the art, the converter 206 converts the analogue signals from the electrodes to machine-readable or digital signals. The output of the analogue-to-digital converter 206 is coupled to a microprocessor or micro-controller. The micro-controller 208 can be used for data acquisition and can also perform the mathematical calculations described hereinafter. Additionally, the micro-controller 208 controls the apparatus 200 in general.

The micro-controller 208 is also used to set the potential of, for example, electrode 101 with respect to electrode 102 through a digital-to-analogue converter 210.

Further, the micro-controller 208 is electrically coupled to a communications port 212 (e.g. RS232, RS485 or HART etc) so that the apparatus 200 can communicate the results of the calculations, the measured values etc to an external apparatus (e.g. a computer, laptop etc). The communications port 212 can be used to provide access to a storage device (e.g. a hard disc or other such memory). It will be appreciated that the micro-controller 208 can provide this function where the controller 208 includes on-board memory.

It will be appreciated that the apparatus 200 includes all the necessary power supplies, voltage regulators etc that are required to operate the components within the apparatus 200.

The apparatus 200 preferably has the capability to select which particular communication protocol is to be used.

Referring to FIG. 4, the current response and potential response (i.e. the raw data) is analysed. Typically, two or more modes of operation are employed, the modes including, but not restricted to, noise analysis where the potentiostat is set to 0V (that is inputs 107, 207 and 307 in FIGS. 1 to 3 are set to 0V) during measurements, and harmonic analysis, where a sinusoidal signal (V sin ωt) is applied to the inputs 107, 207 and 307. The sinusoidal signal (V sin ωt) is a low frequency (typically less than 1 Hz), low amplitude (typically in the order of 20 to 60 millivolts (mV) peak to peak) sine wave perturbation, where V is the maximum voltage amplitude and ω is 2πf, f being the frequency, typically around 0.01 Hz, but can be between 0.001 to 0.1 Hz, although values outwith these ranges may also be used. The solution resistance (e.g. the resistance of the fluids within the pipeline 106, 206, 306) can also be measured by applying a square wave input to the inputs 107, 207, 307 with a frequency of greater than or equal to 2 kHz.

For harmonic distortion and electrochemical noise analysis it is usually advantageous to have a three identical electrode cell, such as that shown in FIG. 1. With three electrodes, it is possible to measure both current and potential noise. Two electrodes may be used (such as the cells shown in FIGS. 2 and 3) provided the electrodes are of substantially different areas (one electrode being in the order of 10 times the area of the second electrode or more). Having one electrode smaller than the other means that the current response is essentially controlled by the smaller of the two electrodes. This facilitates harmonic distortion analysis because if the electrodes were of the same size, then the second harmonic content would tend towards zero and this could give erroneous values for the corrosion current and also the Stearn-Geary constant B. Each electrode will notionally have the same impedance, but as this is a function of area, there is less current density in the smaller of the electrodes, resulting in a reduction in the capability to conduct electricity.

Harmonic analysis is carried out as prescribed by Meszaros[5-7] et al, i.e. the first, second and third harmonic components of current are measured. The advantage of the harmonic analysis technique over other electrochemical measurements is in the derivation of corrosion current ($I_{corr}$), the Tafel coefficients ($b_a$ and $b_c$) and the Stern-Geary constant (B).

Harmonic analysis operates optimally when the corrosion processes are relatively "steady-state", i.e. when the anodic and cathodic processes are stable during the measurement cycle, even if the processes are asymmetrical due to localised corrosion.

Electrochemical noise analysis can be used to identify periods of instability in the corrosion process(es) such as those that occur due to pitting, stress corrosion cracking and other localised corrosion phenomena. In combination, the two measurement techniques (i.e. electrochemical noise and harmonic analysis) provide a powerful tool for the discrimination between general and localised corrosion phenomena.

An advantage of the present invention is that the same set of electrodes can be used to perform both harmonic distortion analysis and electrochemical analysis. It is preferred that the electrodes are all of the same material, and preferably the same material as the plant.

The electrochemical noise analysis can be done using any conventional technique. As can be seen from FIG. 4, both the current and potential responses are statistically analysed using conventional electrochemical noise techniques to provide the first, second, third and fourth moments of the signals, and also the standard deviation, skewness and kurtosis of the signals.

Using the embodiment shown in FIG. 1 as an example, harmonic analysis is carried out on the current response by applying a sinusoidal signal (V sin ωt) to the input 107. A current response ($I_m$), that is the current flowing in the three-electrode cell, is then obtained by measuring the voltage across resistor 109 using a high-resolution (in the order of 20 bits or more) analogue-to-digital convertor. As the sine wave input signal typically has a frequency in the order of 0.01 Hz, this has a period of 100 seconds, and thus samples are taken over a 100 second time period (typically at a rate of 1 per second although higher or lower resolutions may be used).

It will be appreciated that a practical constraint is to apply a sine wave of sufficient amplitude to produce a measurable second harmonic content but not to excessively disturb the system, as in general the second harmonic content may be hidden or obscured within the noise level of the instrumentation used.

Both the DC (that is the polarisation resistance $R_p$) and ac (that is the charge transfer resistance $R_{ct}$) methods of estimating the corrosion current $I_{corr}$ use the Stern-Geary approach that assumes that the potential/current (E/I) plot is linear at the corrosion potential $E_{corr}$. However, analysis of corrosion kinetic theory shows that there is always a curvature of the E/I plot; the degree of curvature depends on the Tafel coefficients ($b_a$, $b_c$). Thus, applying a small ac sinusoidal voltage to a corroding electrode will produce a current response ($I_m$) that comprises the fundamental harmonic (the impedance measurement) and upper harmonics. Measurement of the fundamental and two of the harmonics (e.g. the second and third) allows values of $I_{corr}$ and the Tafel coefficients ($b_a$, $b_c$) to be estimated (i.e. solve three equations using three sets of data to give the three unknowns).

The first harmonic content of the signal is defined as $$I_m \sin 2\pi ft \qquad (1)$$

and this can be plotted against time. The first harmonic $H_1$ is defined as the average value of the first harmonic content and can be calculated by using equation 1 above. That is, a processor (e.g. micro-controller 208), computer or the like can be used to multiply each value of the measured current $I_m$ by sin $2\pi ft$, where f is 0.01 Hz and t is each time period when a sample of raw data is taken. All the calculated values are then added together and divided by the total number of samples taken to provide the average value (i.e. the first harmonic content $H_1$).

The second harmonic $H_2$ is calculated using twice the frequency (i.e. the equivalent of f=0.02 Hz) and the second harmonic content of the signal is given by $$-I_m \cos(2)(2\pi ft) \qquad (2)$$

The second harmonic $H_2$ is thus the average value of the calculations using equation 2 above, using the measured values of $I_m$, f=0.01 Hz and the method described above. Again, the results can be plotted.

Following from this, the third harmonic $H_3$ is calculated using three times the frequency (i.e. the equivalent of f=0.03 Hz) and thus the third harmonic content of the signal is given by $$-I_m \sin(3)(2\pi ft) \qquad (3)$$

The third harmonic $H_3$ is thus the average value of the calculations using equation 3 above, using the measured values of $I_m$, f=0.01 Hz and using the method as described above. Again, the results can be plotted.

A simple analysis based on a Fourier series expansion or a Power series expansion of the Volmer equation for the faradaic current can be used, that is $$I_{faradaic} = I_{corr}\left[\exp\left[\frac{\Delta E}{b_a}\right] - \exp\left[\frac{-\Delta E}{b_c}\right]\right] \qquad 4a)$$

which describes the E/I response in detail.

For a sinusoidal input of amplitude $V_{max}$ and frequency ω (i.e. $\Delta E = V_{max} \sin \omega t$) gives equation 4b) below.

The values of $H_1$, $H_2$ and $H_3$ are used to give an estimate of the corrosion current $I_{corr}$, which is a function of $H_1$, $H_2$ and $H_3$. $I_{corr}$ is calculated using the following equation:

$$I_{corr} = \frac{(H_1)^2}{\sqrt{48} \times \sqrt{2(H_1)(H_3) - (H_2)^2}} \qquad 4b)$$

where $H_1$, $H_2$ and $H_3$ are the first, second and third harmonic contents respectively.

It is also possible to derive the Tafel coefficients $b_a$ and $b_c$ from the anodic and cathodic Tafel slopes. The Tafel coefficients $b_a$ and $b_c$ are a function of $H_1$, $H_2$, $I_{corr}$ and the applied voltage $V_{max}$, and can be calculated using the following equations:

$$\frac{1}{b_a} = \frac{1}{2V_{max}}\left[\frac{H_1}{I_{corr}} + \frac{4H_2}{H_1}\right] \qquad 5)$$

and $$\frac{1}{b_c} = \frac{1}{2V_{max}}\left[\frac{H_1}{I_{corr}} - \frac{4H_2}{H_1}\right] \qquad 6)$$

Equations 4b), 5) and 6) above can be calculated to provide the three unknowns $I_{corr}$, $b_a$, $b_c$ using the values of the first, second and third harmonic contents ($H_1$, $H_2$, $H_3$). However, the above analysis is only applicable to steady-state activation or charge transfer controlled systems, but it may also be used in the presence of a second relaxation due to absorption since only the lower frequency values measured below the charge transfer relaxation become distorted. Experimental evidence shows that the method appears to be useful in any system exhibiting some charge transfer contribution and provided the measurement frequency is restricted to this region. The very low frequency is chosen since the faradaic distortion is only due to the real part of the impedance (i.e. there should be no measurable distortion in the imaginary part of the response).

A feature of the method is that the value of Icorr, the Tafel coefficients and the Stern-Geary constant B in the equation $I_{corr}=B/R_{ct}$ can be obtained simultaneously. Thus, if the Tafel slopes change with time, this can be allowed for in the corrosion test data.

Additionally, the effects of IR drops in the measured system are not apparent because the estimate of $I_{corr}$ relies solely on the observed current flow and not on the applied perturbing voltage (particularly if measurements are made using a three-electrode cell). The IR drops are essentially incorporated into the estimates of the Tafel slopes (i.e. $b_a$, $b_c$) and thus the Stern-Geary constant B.

The Tafel coefficients $b_a$ and $b_c$ are used to derive a value for the Stern-Geary constant B. The Stern-Geary constant B is not strictly a constant but can vary, and it typically has a value of around 0.03 V. The Stern-Geary constant B can be calculated using $$B = \frac{(b_a b_c)}{(b_a + b_c)} \qquad 7)$$

It is conventional in the art to use an approximate value of B as being 0.03 V, but the method of the present invention includes the use of harmonic analysis, and allows the value of B to be calculated more precisely for each system, thus leading to a better indication of the corrosion mechanism and/or the extent of corrosion. This is because the harmonic analysis allows the Tafel coefficients $b_a$ and $b_c$ to be obtained and these can be used to calculate B more precisely using equation 7) above.

$I_{corr}$, the corrosion current, can also be derived from the Stern-Geary constant B and a polarisation resistance $R_p$, and is given by $$I_{corr} = \frac{B}{R_P} \qquad 8)$$

The polarisation resistance $R_p$ is equivalent to the noise resistance $R_n$, and can be calculated by dividing the standard deviation of the potential noise signal by the standard deviation of the current noise signal, both of these typically being obtained using conventional electrochemical analysis techniques.

Having a three-electrode cell arrangement is preferable as it allows the use of harmonic analysis and electrochemical noise analysis to be performed. Use of the three-electrode cell as shown in FIG. 1 allows the data acquisition and analysis to be multiplexed, typically using alternate electrochemical noise and harmonic analysis techniques. For example, if harmonic noise analysis is being used with a frequency f=0.01 Hz, then this equates to a 100 second time period. Thus, electrochemical noise analysis may be done first for a specific time period of say, 300 seconds for example, followed by 100 seconds of harmonic analysis. This can optionally be followed up with further time periods for making other measurements, such as 30 seconds for solution resistance measurements.

During these time periods, raw data can be collected that is used in the electrochemical analysis and in the harmonic analysis as described above. Thereafter, or even during the time periods, the raw data can be analysed as described above with reference to FIG. 4. That is, the current and potential response (outputs 100 and 111 in FIG. 1) are measured with the applied voltage to electrode 101 set to 0V. Thereafter, the sine wave is applied using means 107 and the voltage across resistor 109 is measured to give an indication of the measured current $I_m$. Each of these measurements are typically taken as periodic samples over the time period (e.g. one sample per second) and can be stored as a raw data file on a computer for example.

As the computer (e.g. micro-controller 208) that is linked to the analogue-to-digital analogue converter (e.g. converter 206 via interface 202) coupled across resistor 109 is taking samples, it can be used to calculate the first, second, third and fourth moments of both the current and potential noise signals, and also the standard deviation, skewness and kurtosis of both signals. Also, the computer can calculate the harmonic components $H_1$, $H_2$ and $H_3$ as described above. The computer or the like can also be used to do a number of comparisons of the measured values, as described below and with reference to FIGS. 5a to 5d that show typical comparisons of interest.

Figure 5A:
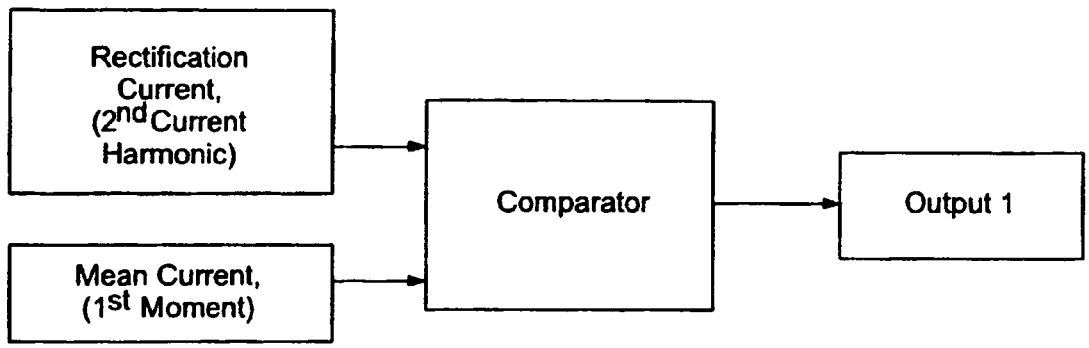
FIG. 5a is a schematic representation of a comparison of a rectification current and a mean current to give an output 1.

FIG. 5a uses a comparator to compare the rectification current (the equivalent of the second harmonic $H_2$) derived from harmonic analysis with the mean current (the first moment of the current) derived from the electrochemical noise technique. This provides a means of discriminating between general and localised corrosion. For general corrosion processes, the two values should be approximately equal in amplitude. When localised corrosion occurs, the absolute value of the mean current will be substantially greater than the absolute value of the rectification current.

Figure 5B:
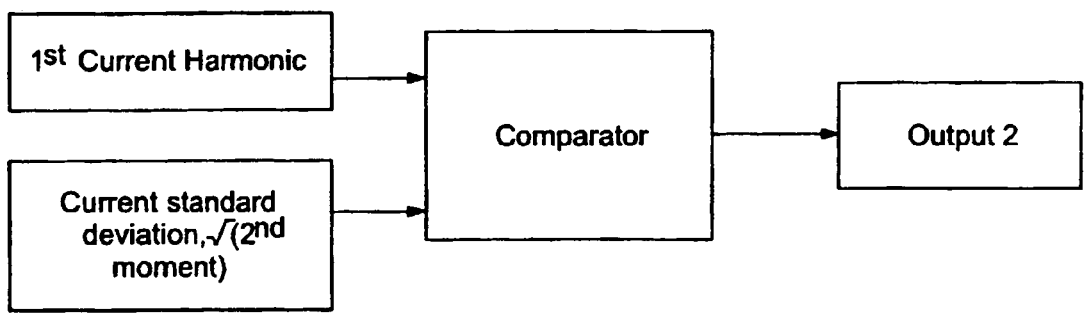
FIG. 5b is a schematic representation of a comparison of a first harmonic current and a current standard deviation to give an output 2.

FIG. 5b uses a comparator to compare the first (fundamental) harmonic current ($H_1$) with the standard deviation of the current noise signals (square root of the second moment), obtained using electrochemical noise techniques. This also provides a means of discriminating between general and localised corrosion. When the first harmonic current is substantially greater than the standard deviation of the current, this would indicate stable corrosion processes associated with general corrosion. As the ratio decreases, the probability of localised corrosion increases.

Figure 5C:
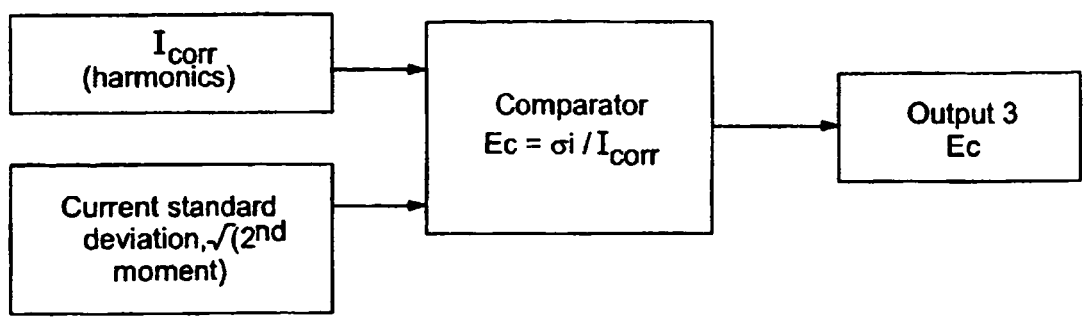
FIG. 5c is a schematic representation of a comparison of a corrosion current and a current standard deviation to give an output 3.

FIG. 5c uses a comparator to compare the current standard deviation (square root of the second moment) with the corrosion current ($I_{corr}$) derived from harmonic analysis ($H_1$, $H_2$, $H_3$). This also provides a means of discriminating between general and localised corrosion and additionally gives a factor $E_c$. The factor $E_c$ is thus given by $\sigma I/I_{corr}$. During general corrosion processes the corrosion current is typically several orders of magnitude greater then the standard deviation value (typically greater than or equal to 1000 times larger). When localised corrosion occurs, the standard deviation value will approach the value of the corrosion current.

Figure 5D:
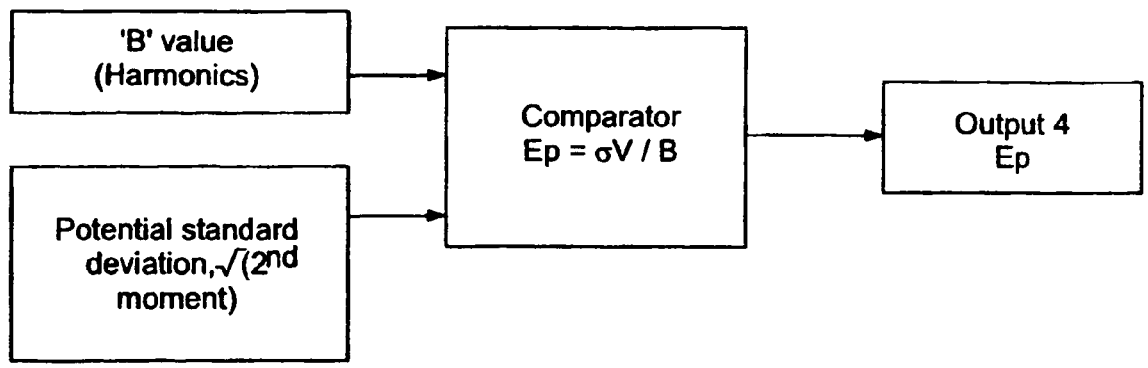
FIG. 5d is a schematic representation of a comparison of a Stern-Geary constant and a potential standard deviation to give an output 4.

In FIG. 5d, a comparator is used to compare the Stern-Geary constant B derived from harmonic analysis with the standard deviation of potential (that is the square root of the second moment of the potential noise signal). This also provides a means of discriminating between general and localised corrosion and additionally gives a factor $E_p$. The factor $E_p$ is thus given by $\sigma V/B$. During general corrosion processes the measured B value will be several orders of magnitude greater than the standard deviation of potential (typically greater than or equal to 1000 times larger). When localised corrosion occurs, the standard deviation will approach the value of B.

This comparison may only be made if both the B value and the potential noise are measured, and is generally limited to three-electrode operation (that is using the arrangement of the electrodes shown in FIG. 1). In two electrode mode (that is using the arrangements shown in FIGS. 2 and 3) it is possible to measure the B value using the apparatus described, whereas the potential noise measurement typically requires the presence of a third electrode.

The comparisons drawn in FIGS. 5c and 5d are based on the relationships:

$$I_{corr} = \frac{\sigma I \times B}{\sigma V} \qquad 9)$$

where $I_{corr}$ is the corrosion current density determined from harmonic analysis (amps per cm$^2$);

σI is the standard deviation of the current (amps per cm$^2$) from noise analysis;

B is the Stern-Geary factor derived from harmonic analysis; and

σV is the standard deviation of potential from noise analysis.

Rearranging equation 9 above gives $$\frac{\sigma I}{I_{corr}} = \frac{\sigma V}{B} = E \quad \quad 10)$$

where E is a constant. The constant E may be derived from either knowledge of σI/$I_{corr}$ ($E_c$) or from σV/B ($E_p$) (or both), when the values of $I_{corr}$ and B are measured independently from σI and σV. It is expected that these values will be equal in amplitude, provided that the transfer function between σV and σI is linear or approximately linear.

$I_{corr}$ can also be derived from the Stern-Geary constant B and a polarisation resistance $R_p$ or noise resistance $R_n$. The polarisation resistance $R_p$ and the noise resistance $R_n$ are equivalent to one another, and are given by $$R_P = \frac{\sigma V}{\sigma I} = R_n \quad \quad 11)$$

from Ohm's Law. Thus, substituting $R_p$ or $R_n$ for (σV/σI) in equation 9 above gives $$I_{corr} = \frac{B}{R_P} = \frac{B}{R_n} \quad \quad 12)$$

This provides a further alternative for calculating the corrosion current $I_{corr}$.

It has been discovered that the composite value of the constant E (that is $E_c$ and $E_p$), a system dependant constant, essentially characterises the corrosion processes and is fundamentally different for localised and general corrosion processes in the frequency band of interest.

For general corrosion processes (uniform material wastage), for example mild steel corroding in dilute acid, the values of $E_c$ and $E_p$ are typically equal and have been determined as having low values typically 0.001.

For localised corrosion processes (pitting), for example 316 stainless steel in hypochlorite solution, the values of $E_c$ and $E_p$ are much greater by several orders of magnitude.

Because it is now possible to determine all the variables, it is possible to derive a value for this system dependant constant E and use this to determine an improved estimate of the corrosion penetration.

Figure 5E:
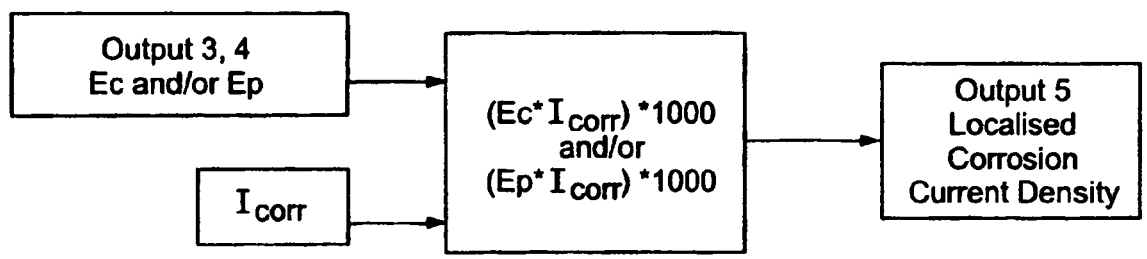
FIG. 5e is a schematic representation of a comparison of output 3 of FIG. 5c and/or output 4 of FIG. 5d with a corrosion current to give an output S.

FIG. 5e illustrates how the improved knowledge of outputs $E_c$ and $E_p$ (i.e. E) can be used to provide an estimate of the localised corrosion penetration rate. It is important that both electrochemical noise and harmonic analysis are used to derive these relationships as one single technique alone cannot generally achieve these comparisons. This is because the standard deviations of the current and potential noise signals, that is σI and σV are typically derived from electrochemical noise analysis, and the Stern-Geary constant B and the corrosion current $I_{corr}$ are typically derived from harmonic analysis.

The corrosion rate of the electrodes is calculated from the corrosion current density $I_{corr}$ (amperes per square centimeter), where the area is the area of one electrode. When electrodes of differing surface area are used, the smaller surface area is used in the calculation.

A typical calculation to derive the general corrosion rate in millimeters per year, would be:

$$\text{Corrosion rate} = \frac{I_{corr} \times T \times Awt \times 10}{z \times F \times \rho} \quad \quad 11)$$

Where $I_{corr}$ is the corrosion current density in amperes per square centimeter;

T is the number of seconds in one year;

Awt is the atomic mass of the metal in grams;

10 is a conversion of cm to mm;

z is the number of electrons transferred;

F is the Faraday constant; and

ρ is the density of the metal in grams per cubic centimeter.

This gives the general corrosion rate. During localised corrosion, the local penetration rate at the pitting areas will be much greater than the average penetration rate. A method for approximating the local penetration rate is advocated, that is, to correct the general corrosion rate using the improved knowledge regarding the E proportionality factor. For general corrosion (carbon steel in dilute citric acid) this factor has been derived using harmonic and noise analysis as being in the order of 0.001.

It will be apparent that the corrosion rate estimate calculated using equation 11) above is based on a determination of $I_{corr}$ derived from harmonic analysis. As $I_{corr}$ is the corrosion current density in amperes per square centimeter, the calculation is based on data that has been normalised to the whole surface area of the electrode. This is the equivalent of general corrosion, which assumes that the electrode corrodes uniformly over the entire surface area of the electrode. However, this is not the case for localised corrosion, where the electrode would corrode at a specific point or points on the surface area that, in time, typically develop into pits in the surface of the electrode.

The values of $E_c$ and $E_p$ are typically around 0.001 for general corrosion. However, the more these values deviate from 0.001, the smaller the area of corrosion. This is because the composite value E (the equivalent of $E_c$ and $E_p$) is related to $I_{corr}$ by equation 10) above, that is E=σI/$I_{corr}$. As $I_{corr}$ is proportional to the surface area, then dividing $E_p$ or $E_c$ by 0.001 (that is the value for general corrosion), and multiplying this by $I_{corr}$ (as shown in FIG. 5e), modifies $I_{corr}$ by multiplying by a scaling factor that takes into account the fact that the corrosion may be at a local point, rather than spread over the entire surface area of the electrode.

That is, if the calculated values of $E_c$ and $E_p$ are close to 0.001, then this scaling factor (e.g. $E_c$/0.001) would not modify $I_{corr}$ to any substantial extent, thus indicating that general corrosion was present. However, if the calculated values of $E_c$ and $E_p$ are very much greater than 0.001, then the scaling factor (e.g. $E_c$/0.001 or the equivalent $E_c$*1000) could have a significant effect on $I_{corr}$. The farther that the values of $E_c$ and $E_p$ deviate from 0.001, the more localised the corrosion will be and thus the scaling factor will give an improved estimate of $I_{corr}$ that takes into account the possibility of the corrosion being localised to a particular small surface area, rather than being an average value of the corrosion over the entire surface area. In this way, the calculations to derive $I_{corr}$ are modified by the scaling factor so that it is possible to determine between general and localised corrosion.

Figure 6:
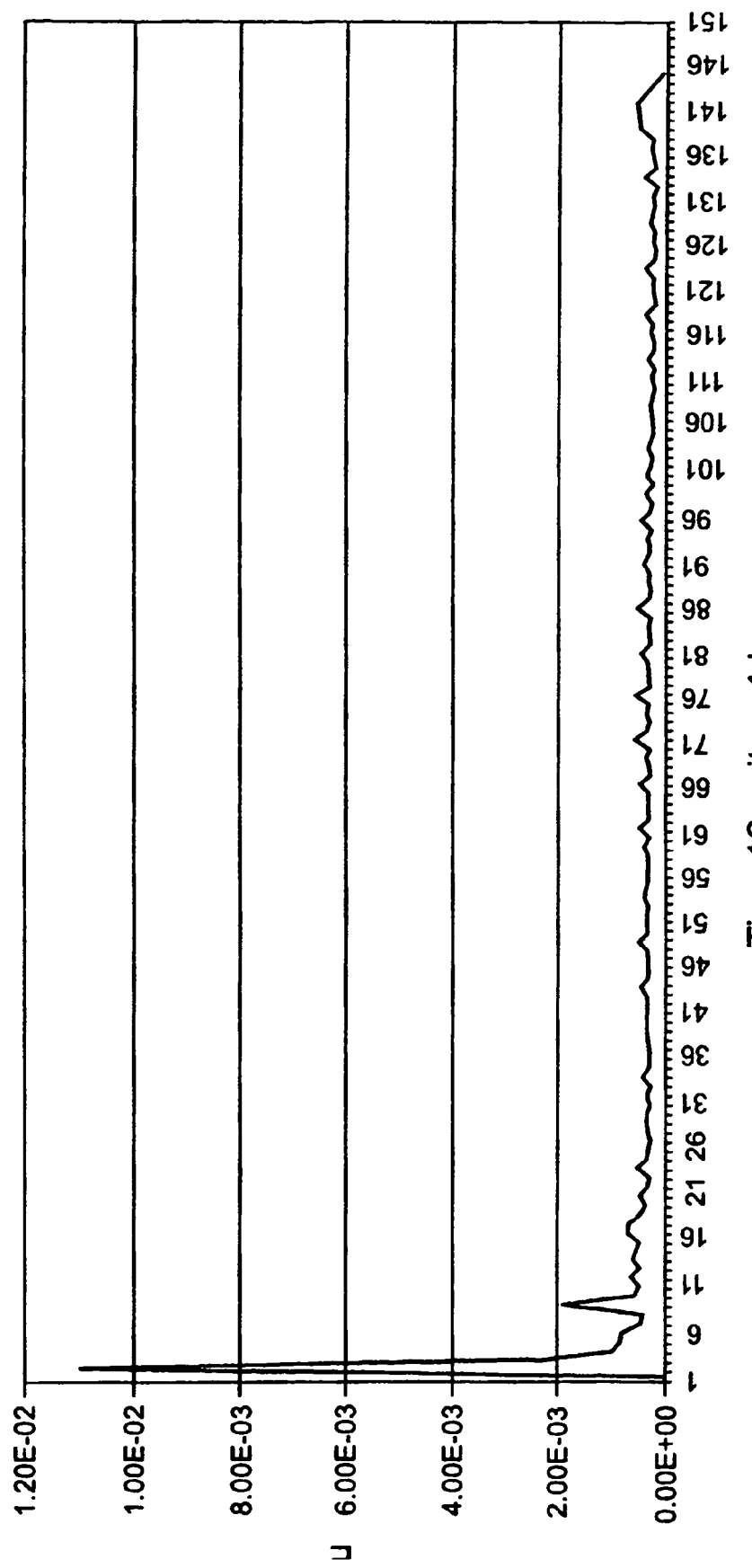
FIG. 6 is a graph of a factor E against time for the general corrosion of mild steel in dilute citric acid.

FIG. 6 illustrates data obtained for this factor E for the general corrosion of mild steel in dilute citric acid at room temperature. During such general corrosion the value of E rapidly stabilises. The data obtained and shown in FIG. 6 is indicative of general corrosion and the values of $E_p$ and $E_c$ are the outputs of the comparators of FIGS. 5c and 5d.

Figure 7:
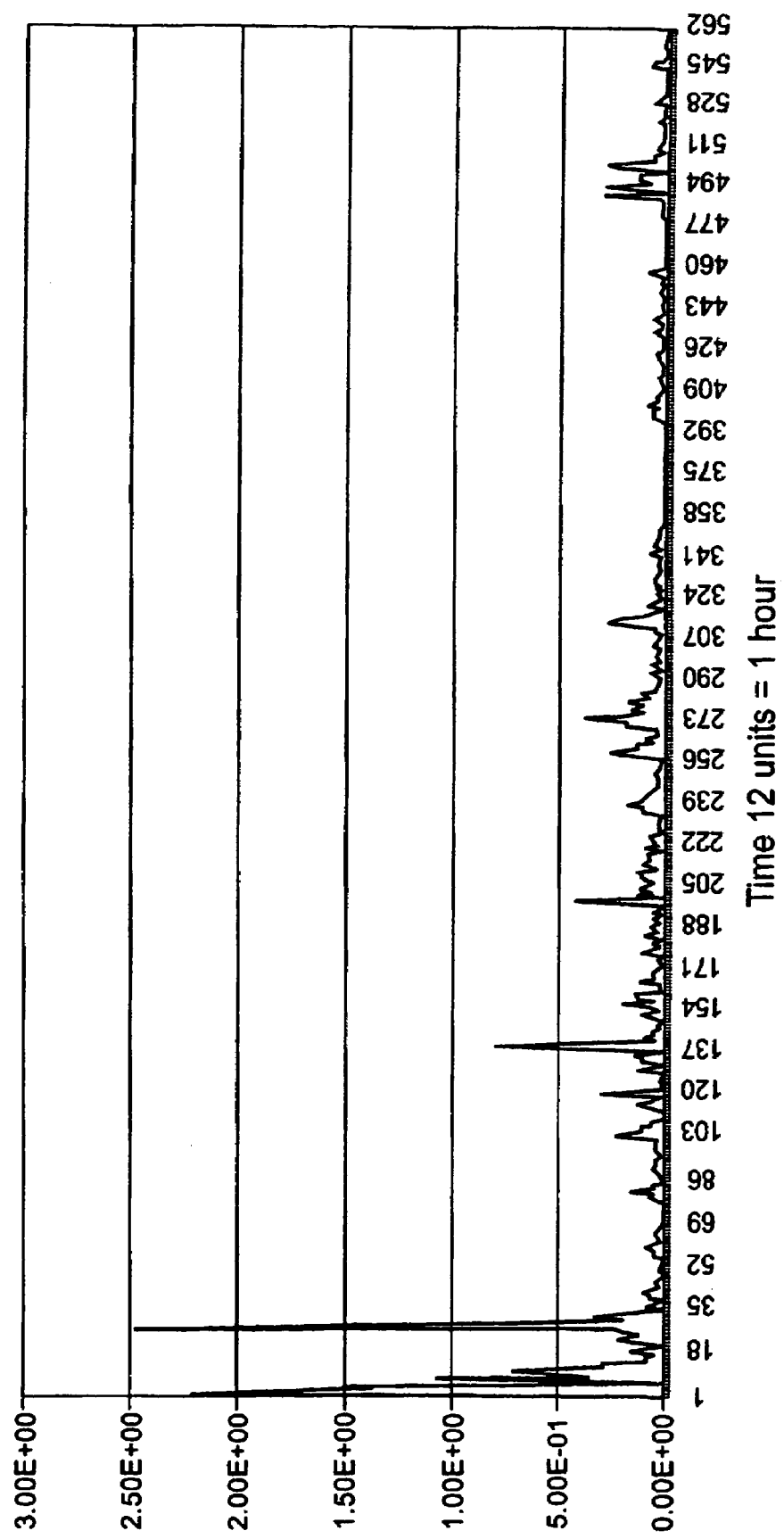
FIG. 7 is a graph of a factor E against time for the pitting corrosion of stainless steel in hypochlorite solution.

By comparison, FIG. 7 illustrates the values obtained for stainless steel (316L) in hypochlorite solution. It can be seen that the values obtained in this instance are much higher due to the occurrence of localised (pitting) corrosion. The data in FIG. 7 is indicative of localised corrosion and the values of $E_p$ and $E_c$ are the outputs of the comparators of FIGS. 5c and 5d.

Figure 8:
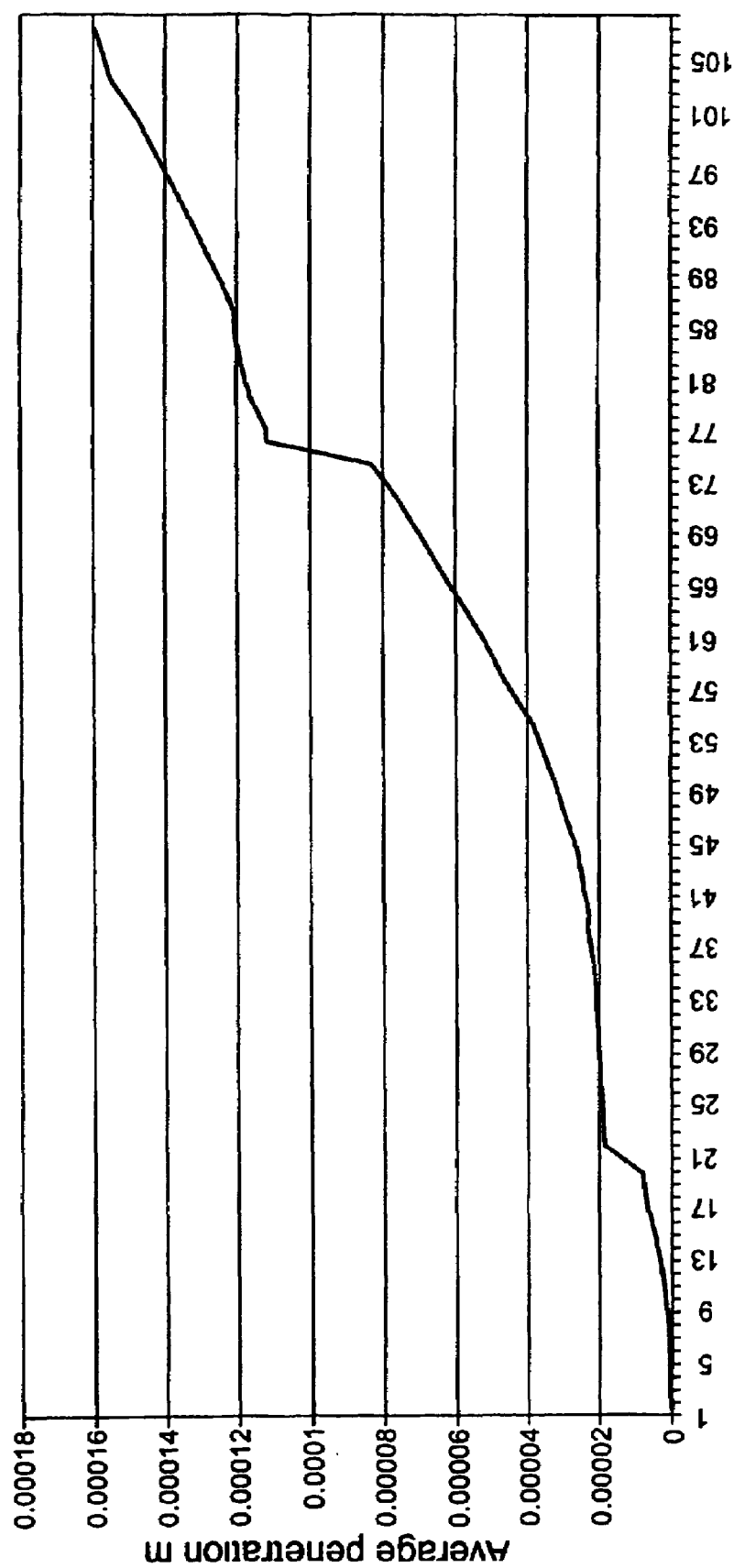
FIG. 8 is a graph of an average penetration against time for general corrosion of stainless steel in hypochlorite solution.

FIG. 8 illustrates the general corrosion cumulative corrosion calculated using data normalised to an area of 1 square centimeter (i.e. assuming general corrosion) that severely underestimates the localised pit penetration rate. This is because FIG. 8 illustrates the general corrosion rate rather than localised corrosion, and the general corrosion rate is calculated based on the entire surface area of the sample rather than on a localised scale. FIG. 8 shows the expected material loss if the corrosion were general in nature. During the period of exposure to the corrosive conditions, the general corrosion loss after 9 hours is estimated to be 0.00016 millimeters, which corresponds to no visible change and thus there would be no apparent visible loss. Indeed, a visual inspection of the sample indicated that significant pits had developed after 9 hours, indicating that there was significant localised (pitting) corrosion. This localised corrosion was not detected as the test was based on general corrosion and thus took into account an average corrosion rate over the entire surface area of the sample.

Figure 9:
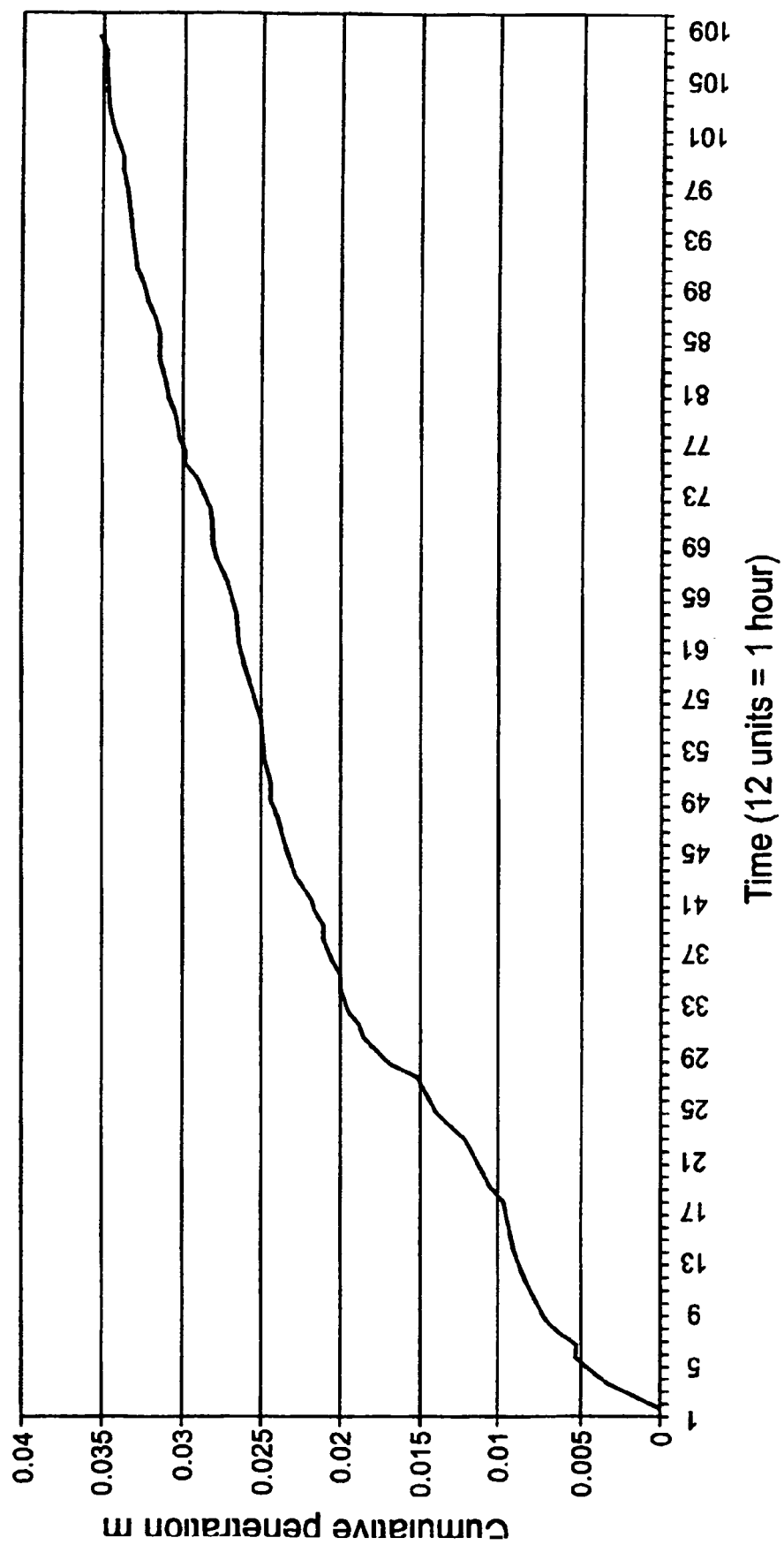
FIG. 9 is a graph of a cumulative penetration against time for the data of FIG. 8 that has been modified to take account of localised corrosion as illustrated in FIG. 5e.

If however, the data plotted in FIG. 8 is modified, by taking into account the higher values of $E_c$ or $E_p$ (that are indicative of localised corrosion) by multiplying the general corrosion rate estimate by the scaling factor (e.g. by multiplying $E_c$ by 1000 or by multiplying $E_p$ by 1000), a much improved estimate of localised penetration may be obtained (see FIG. 9).

FIG. 9 illustrates the data obtained for FIG. 8, modified to take into account the localised penetration using the data presented in FIG. 7. By modifying the corrosion rate estimate to take into account localised corrosion as illustrated in FIG. 5e, the localised penetration (by integration of the rate estimate) after 9 hours is estimated as 0.035 millimeters, which corresponds to the development of visible pits.

Figure 10:
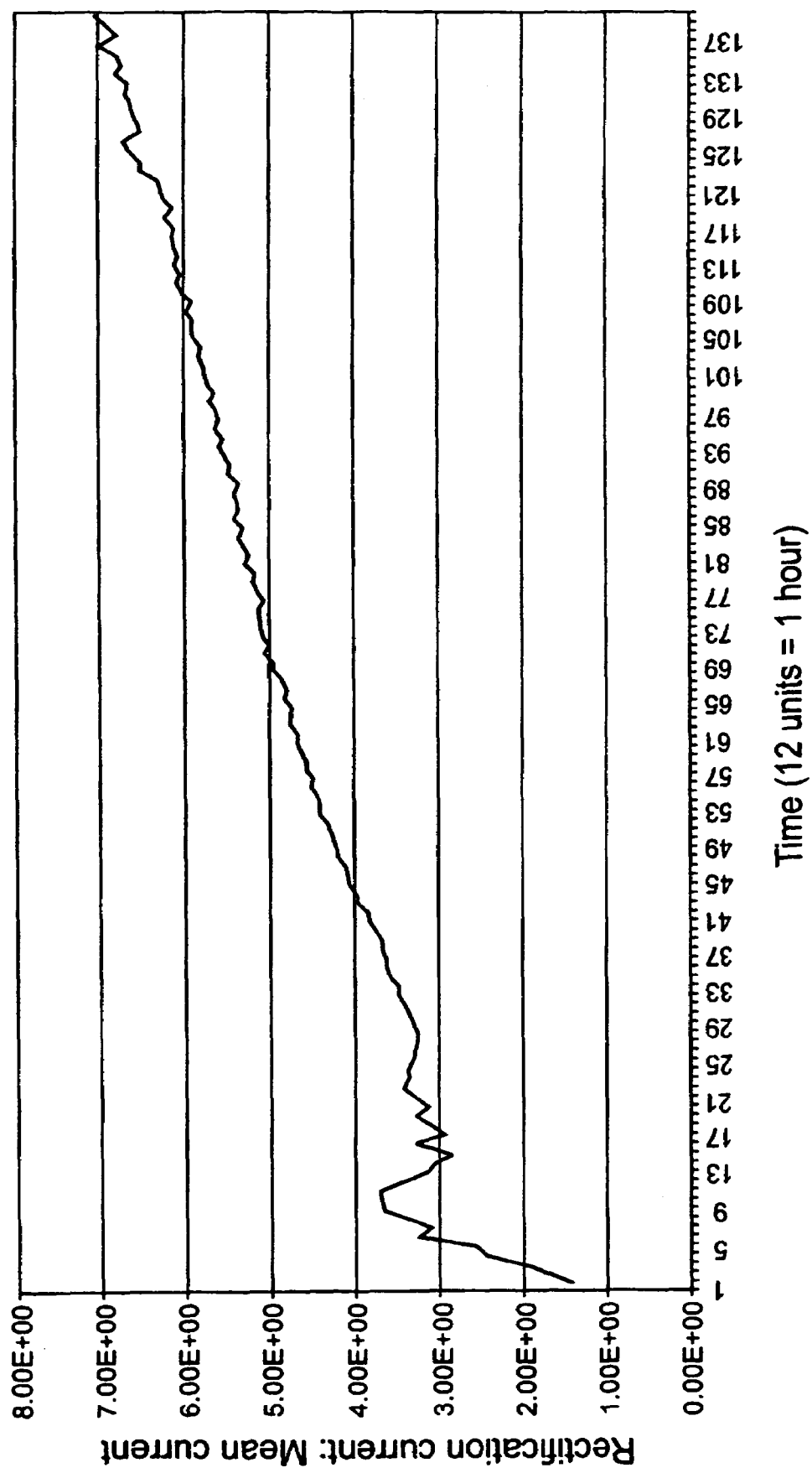
FIG. 10 is a graph of output 1 of FIG. 5a against time for a system undergoing general corrosion.

FIG. 10 illustrates the ratio obtained for the rectification current to mean current (FIG. 5a) for a system undergoing general corrosion. As the corrosion rate stabilises the value of output 1 achieves a value between five and seven.

Figure 11:
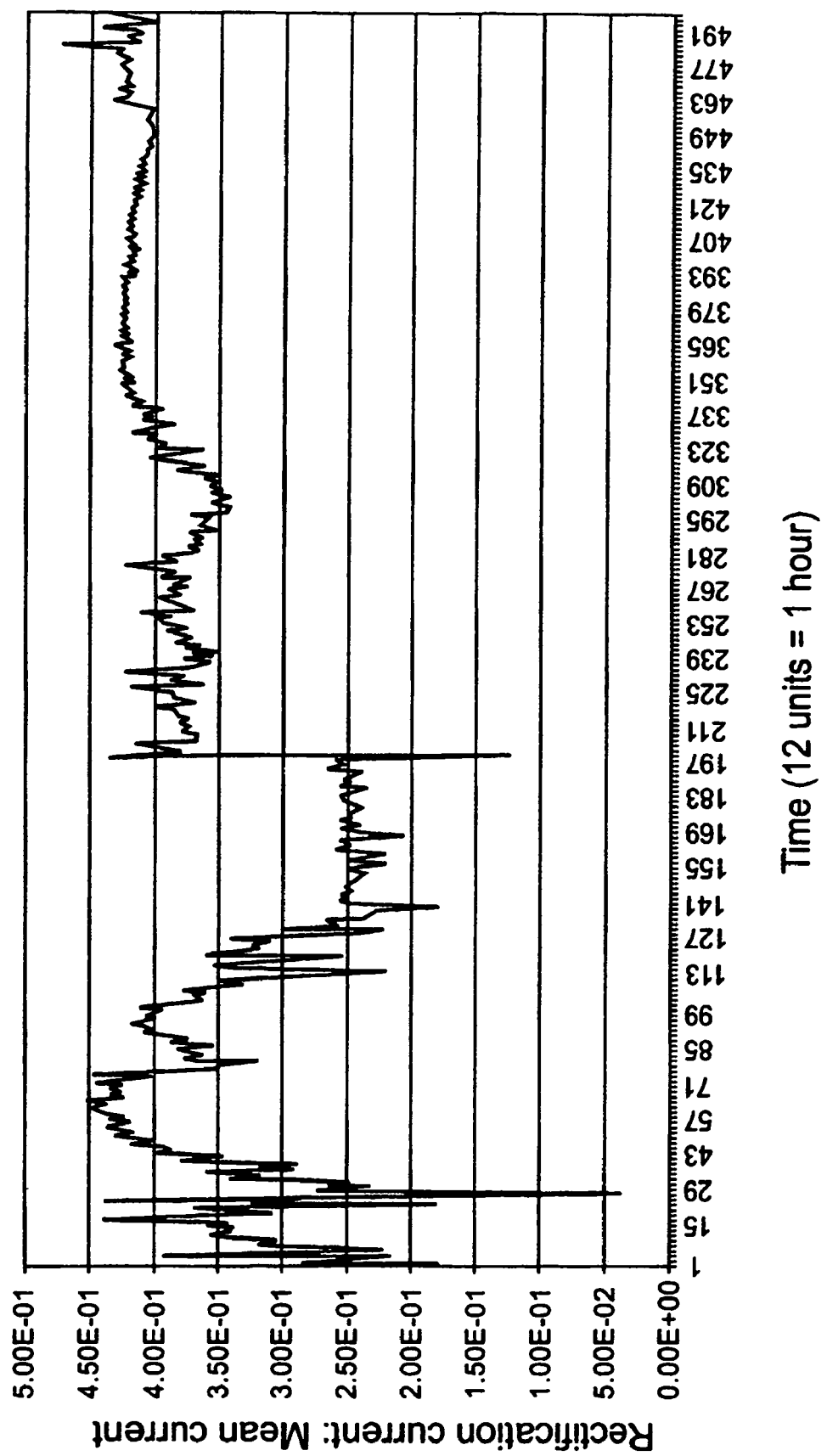
FIG. 11 is a graph of output 1 of FIG. 5a against time for a system undergoing pitting corrosion.

By comparison to FIG. 10, FIG. 11 illustrates output 1 (FIG. 5a) for a system undergoing localised, pitting corrosion. It can be seen that the values obtained for the rectification compared to the mean current are substantially lower in this instance, typically around 0.4.

The value of $I_{mean}$ typically stabilises and it is expected that the ratio of $H_2$ to $I_{mean}$ would give comparatively large numbers for general corrosion, and this would change to comparatively small numbers for localised corrosion, as supported by the values obtained using the data in FIGS. 10 and 11.

Figure 12:
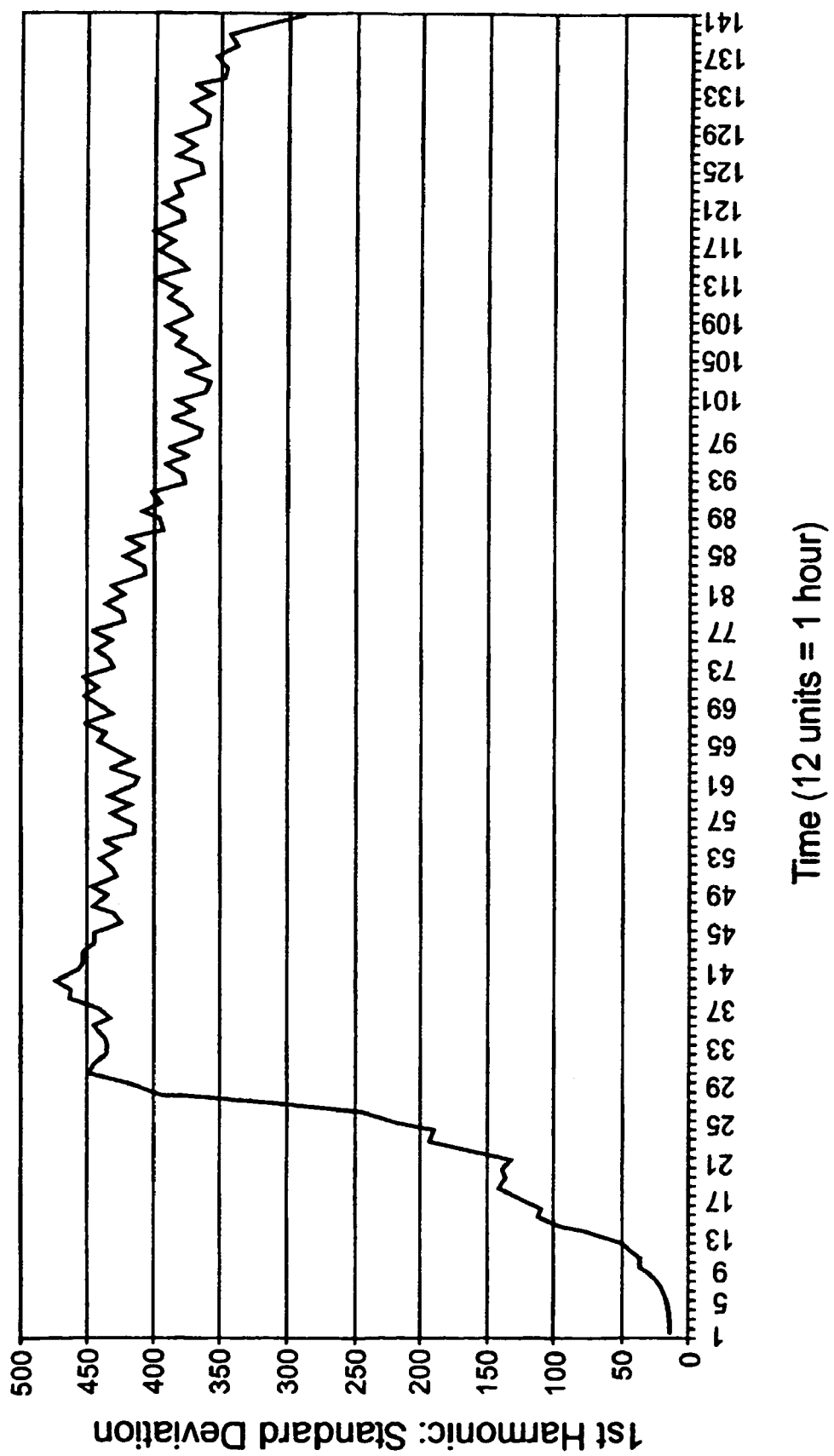
FIG. 12 is a graph of output 2 of FIG. 5b against time for a system undergoing general corrosion.

FIG. 12 shows the progression of output 2 (the comparison of the fundamental harmonic current with the standard deviation of the current in FIG. 5b) for general corrosion. The ratio is seen to stabilise at a high value of around 300 to 400. The data shows that the noise current is substantially smaller than the first (fundamental) current harmonic, indicating that general corrosion is present.

Figure 13:
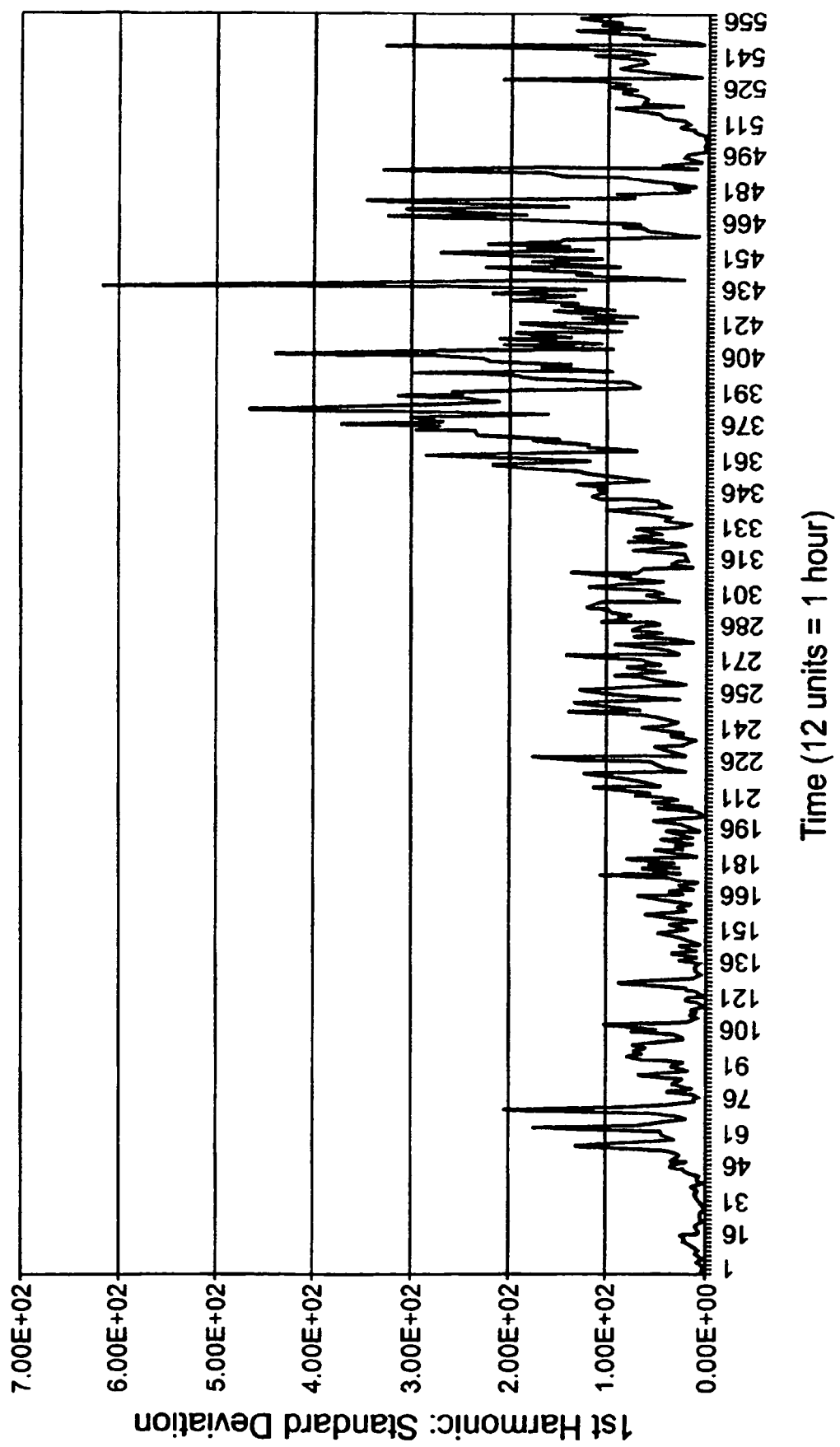
FIG. 13 is a graph of output 2 of FIG. 5b against time for a system undergoing pitting corrosion.

By comparison to FIG. 12, FIG. 13 illustrates the progression of output 2 (FIG. 5b) during pitting corrosion. The output is much more unstable, particularly during pit initiation where the value tends to be at a much lower value (typically less than 100) than that obtained for general corrosion (see FIG. 12 for comparison). In this case, the noise current is becoming a significant proportion of the first (fundamental) harmonic current, indicating localised corrosion.

Figure 14:
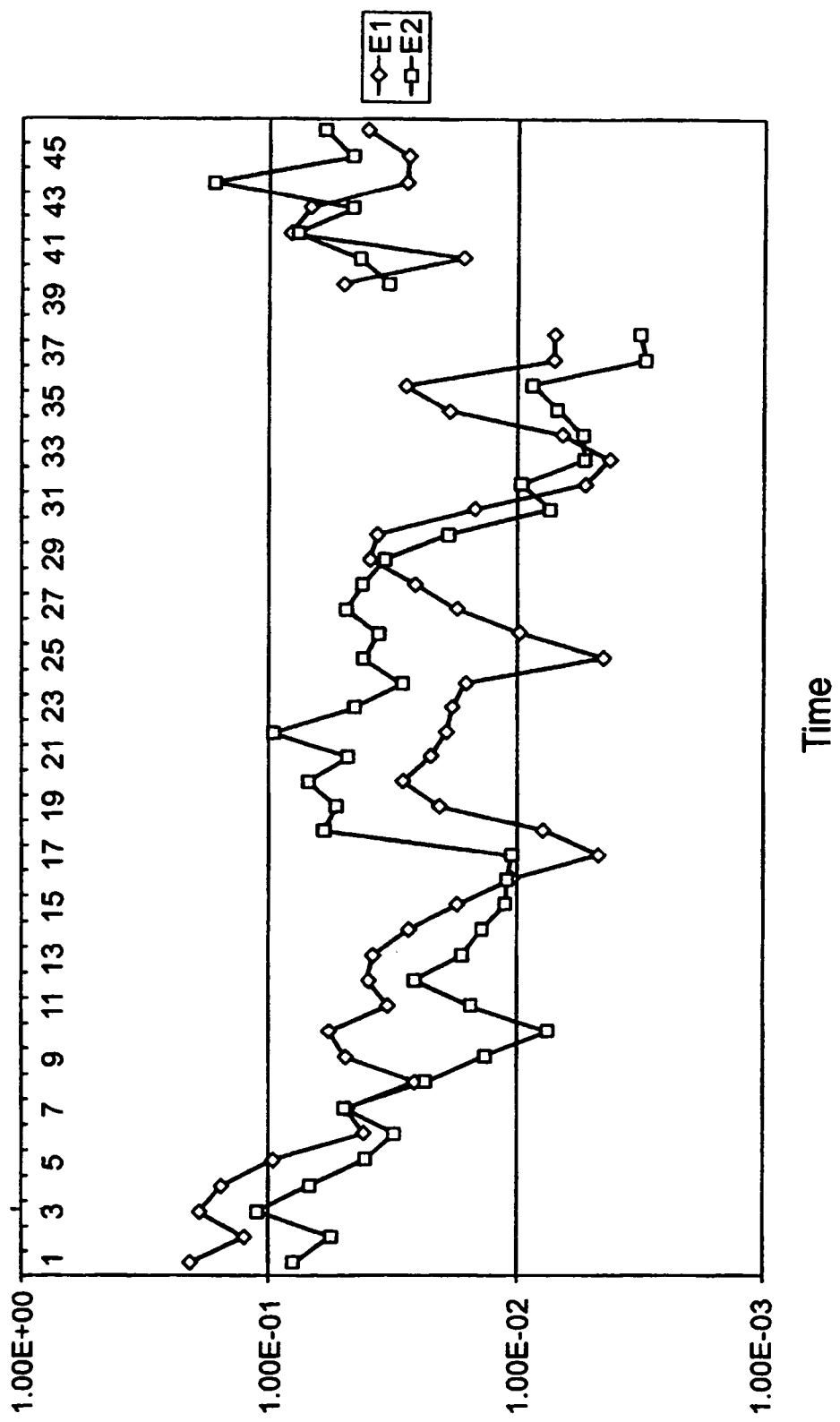
FIG. 14 is a graph of factors $E_c$ and $E_p$ against time for a system undergoing pitting corrosion.

FIG. 14 illustrates the factors $E_c$ and $E_p$ derived for the pitting corrosion example, showing how the values track closely and have similar values.

An advantage of the present invention is its sensitivity to the mode of corrosion, thus enabling a means of identification and/or control of general and localised corrosion.

A further advantage of the present invention is its speed of response to changes in corrosion rate and mechanism to allow monitoring in real time.

Modifications and improvements may be made to the foregoing without departing from the scope of the present invention.

REFERENCES

1. Hladky U.S. Pat. No. 4,575,678
2. Eden U.S. Pat. No. 5,139,627
3. Martinchek U.S. Pat. No. 6,015,484
4. Eden, D. A. and Skerry B. S., ACS Symposium series 322, Polymeric Materials for Corrosion Control, Editors Dickie & Floyd, p. 36-47 (1986)
5. Devay, J., and Meszaros, L., Acta Chim. Acad. Sci. Hungaricae, Vol. 100, No. 1-4, p. 183-202 (1979).
6. Devay, J., and Meszaros, L., Acta Chim. Acad. Sci. Hungaricae, Vol. 104, No. 3, p. 311-316 (1980).
7. Meszaros, L., Korrosion Figyelo, Vol 21, No. 2, p. 30 (1981).

The invention claimed is:

1. A method of assessing corrosion of a metal object, the method comprising the steps of:
    providing the metal object with an electrode assembly capable of generating electrochemical noise signals, the electrode assembly including at least one electrode that is electrically isolated from the metal object;
    periodically sampling the electrochemical noise signals at the free corrosion potential;
    applying a sinusoidal voltage signal to the electrode assembly and obtaining a current response of the electrode assembly; and
    analysing the statistical distribution of the noise signals and a harmonic content of the current response to determine information concerning the corrosion.

2. A method according to claim 1, wherein the method assesses the extent of the corrosion.

3. A method according to claim 1, wherein the method assesses the nature of the corrosion.

4. A method according to claim 1, wherein the method compares the harmonic content of the current response with the statistical distribution of the noise signals.

5. A method according to claim 1, wherein the electrode assembly includes three electrodes.

6. A method according to claim 5, wherein the three electrodes are electrically isolated from one another.

7. A method according to claim 5, wherein a first electrode is maintained at a potential of zero volts with respect to a second electrode during the generation and/or sampling of the electrochemical noise signals.

8. A method according to claim 5, wherein the step of periodically sampling the electrochemical noise signals comprises the step of periodically sampling the potential noise signals and/or the current noise signals.

9. A method according to claim 8, wherein the step of periodically sampling the current noise signal comprises the step of periodically measuring a current flowing between the first electrode and the third electrode.

10. A method according to claim 9, wherein the method includes the additional step of calculating a first, second, third and/or fourth moment of the current noise signal.

11. A method according to claim 10, wherein the method includes the additional step of calculating the kurtosis and/or skewness values of the current noise signal.

12. A method according to claim 10, wherein the step of periodically sampling the potential noise signal comprises the step of periodically measuring a potential difference between the first electrode and the third electrode.

13. A method according to claim 12, wherein the method includes the additional step of calculating a first, second, third and/or fourth moment of the potential noise signal.

14. A method according to claim 13, wherein the signal that is applied to the electrode assembly comprises a low frequency, low voltage sinusoidal wave.

15. A method according to claim 14, wherein the frequency is in the range of 0.001 Hertz to 1 Hertz, and the voltage is in the range of 20 to 60 millivolts peak to peak.

16. A method according to claim 13, wherein the method includes the additional step of calculating a standard deviation of the current noise signal.

17. A method according to claim 16, wherein the method includes the additional step of calculating a standard deviation of the potential noise signal.

18. A method according to claims 17, wherein the method includes the additional step of calculating a corrosion current derived from the harmonic analysis.

19. A method according to claim 18, wherein the method includes the additional step of comparing the corrosion current to the standard deviation of the current noise signal.

20. A method according to claims 17, wherein the method includes the additional step of calculating anodic and cathodic Tafel constants from the harmonic analysis.

21. A method according to claim 20, wherein the method includes the additional step of calculating a Stern-Geary constant from the harmonic analysis.

22. A method according to claim 21, wherein the method includes the additional step of comparing the Stern-Geary constant to the standard deviation of the potential noise signal.

23. A method according to claim 21, wherein the method includes the additional step of calculating a corrosion rate.

24. A method according to claim 21, wherein the method includes the additional step of calculating a factor $E_c$.

25. A method according to claim 24, wherein the step of calculating the factor $E_c$ comprises dividing the standard deviation of the current noise signal by the corrosion current.

26. A method according to claim 24, wherein the method includes the additional step of modifying the value of the corrosion current by multiplying the value by a scaling factor of $E_c/0.001$.

27. A method according to claim 26, wherein the method includes the additional step of re-calculating the corrosion rate using the modified value of the corrosion current.

28. A method according to claim 21, wherein the method includes the additional step of calculating a factor $E_p$.

29. A method according to claim 28, wherein the step of calculating the factor $E_p$ comprises dividing the standard deviation of the potential noise signal by the Stern-Geary constant.

30. A method according to claim 28, wherein the method includes the additional step of modifying the value of the corrosion current by multiplying the value by a scaling factor of $E_p/0.001$.

31. A method according to claim 30, wherein the method includes the additional step of calculating a corrosion rate using the modified value of the corrosion current.

32. A method according to claim 20, wherein the step of calculating the Stern-Geary constant comprises multiplying the anodic and cathodic Tafel constants together, and then dividing by the sum of the anodic and cathodic Tafel constants.

33. A method according to claim 16, wherein the step of analysing the harmonic content includes the additional step of sampling the current response at periodic intervals.

34. A method according to claim 33, wherein the step of analysing the harmonic content includes the step of calculating a first harmonic content, a second harmonic content and/or a third harmonic content of the current response.

35. A method according to claim 34, wherein the step of calculating the first harmonic content includes the additional steps of multiplying the current response obtained at each sample by sin 2πft (where f is the frequency of the signal and t is the time at which the current response was sampled) for each time period; summing all of the multiplications; and dividing by a total number of samples taken.

36. A method according to claim 34, wherein the method includes the additional step of comparing the first harmonic content of the current response with the standard deviation of the current noise signal.

37. A method according to claim 34, wherein the step of calculating the second harmonic content includes the additional steps of multiplying the current response obtained at each sample by −cos(2)(2πft)(where f is the frequency of the signal and t is the time at which the current response was sampled) for each time period; summing all of the multiplications; and dividing by a total number of samples taken.

38. A method according to claim 34, wherein the method includes the additional step of comparing the second harmonic content of the current response with the first moment of the current noise signal.

39. A method according to claim 34, wherein the step of calculating the third harmonic content includes the additional steps of multiplying the current response obtained at each sample by −sin(3)(2πft)(where f is the frequency of the signal and t is the time at which the current response was sampled) for each time period; summing all of the multiplications; and dividing by a total number of samples taken.

40. A method according to claim 12, wherein the method includes the additional step of calculating the kurtosis and/or skewness values of the potential noise signal.

41. A method according to claim 10, wherein the signal is applied between the first electrode and the second electrode.

42. A method according to claim 41, wherein the current response is obtained by measuring a current flowing between the first and the third electrode in response to the applied signal.

* * * * *